(12) United States Patent
Allavatam et al.

(10) Patent No.: US 8,565,878 B2
(45) Date of Patent: Oct. 22, 2013

(54) ACCURATE CARDIAC EVENT DETECTION IN AN IMPLANTABLE CARDIAC STIMULUS DEVICE

(75) Inventors: Venugopal Allavatam, Oceanside, CA (US); Surekha Palreddy, Maplewood, MN (US); Rick Sanghera, San Clemente, CA (US); Jay A. Warren, San Juan Capistrano, CA (US)

(73) Assignee: Cameron Health, Inc., San Clemente, CA (US)

( * ) Notice: Subject to any disclaimer, the term of this patent is extended or adjusted under 35 U.S.C. 154(b) by 1265 days.

(21) Appl. No.: 12/399,901

(22) Filed: Mar. 6, 2009

(65) Prior Publication Data

US 2009/0228057 A1    Sep. 10, 2009

Related U.S. Application Data

(60) Provisional application No. 61/034,938, filed on Mar. 7, 2008.

(51) Int. Cl.
*A61N 1/36* (2006.01)

(52) U.S. Cl.
USPC .................................. 607/28; 607/9; 600/509

(58) Field of Classification Search
USPC .......... 607/9, 8, 27, 4, 28; 600/508, 509, 516, 600/512
See application file for complete search history.

(56) References Cited

U.S. PATENT DOCUMENTS

| | | |
|---|---|---|
| 4,184,493 A | 1/1980 | Langer et al. |
| 4,300,567 A | 11/1981 | Kolenik et al. |
| 4,407,288 A | 10/1983 | Langer et al. |
| 4,450,527 A | 5/1984 | Sramek |
| 4,457,315 A | 7/1984 | Bennish |
| 4,589,420 A | 5/1986 | Adams et al. |
| 4,595,009 A | 6/1986 | Leinders |
| 4,679,144 A | 7/1987 | Cox et al. |
| 4,693,253 A | 9/1987 | Adams |

(Continued)

FOREIGN PATENT DOCUMENTS

| | | |
|---|---|---|
| EP | 0554208 A2 | 8/1993 |
| WO | 2009-111764 A2 | 9/2009 |
| WO | 2009-111764 A3 | 11/2009 |

OTHER PUBLICATIONS

International Preliminary Report on Patentability and Written Opinion of the International Searching Authority, PCT Application PCT/US2009/036432, dated Sep. 7, 2010 (related Foreign Prosecution based on claims in WO2009/111764A2).

(Continued)

*Primary Examiner* — Christopher D Koharski
*Assistant Examiner* — Pamela M Bays
(74) *Attorney, Agent, or Firm* — Schwegman Lundberg & Woessner, P.A.

(57) ABSTRACT

Methods, systems, and devices for signal analysis in an implanted cardiac monitoring and treatment device such as an implantable cardioverter defibrillator. In some illustrative examples, detected events are analyzed to identify changes in detected event amplitudes. When detected event amplitudes are dissimilar from one another, a first set of detection parameters may be invoked, and, when detected event amplitudes are similar to one another, a second set of detection parameters may be invoked. Additional methods determine whether the calculated heart rate is "high" or "low," and then may select a third set of detection parameters for use when the calculated heart rate is high.

16 Claims, 14 Drawing Sheets

(56) References Cited

U.S. PATENT DOCUMENTS

| | | |
|---|---|---|
| 4,750,494 A | 6/1988 | King |
| 4,779,617 A | 10/1988 | Whigham |
| 4,940,054 A | 7/1990 | Grevis et al. |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,117,824 A | 6/1992 | Keimel et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,271,411 A | 12/1993 | Ripley et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,339,820 A | 8/1994 | Henry et al. |
| 5,342,402 A | 8/1994 | Olson et al. |
| 5,342,407 A | 8/1994 | Dahl et al. |
| 5,351,686 A | 10/1994 | Steuer et al. |
| 5,376,104 A | 12/1994 | Sakai et al. |
| 5,423,326 A | 6/1995 | Wang et al. |
| 5,470,342 A | 11/1995 | Mann et al. |
| 5,486,199 A | 1/1996 | Kim et al. |
| 5,513,644 A | 5/1996 | McClure et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,564,430 A | 10/1996 | Jacobson et al. |
| 5,607,455 A | 3/1997 | Armstrong |
| 5,620,466 A | 4/1997 | Haefner et al. |
| 5,658,317 A | 8/1997 | Haefner et al. |
| 5,685,315 A | 11/1997 | McClure et al. |
| 5,702,425 A | 12/1997 | Wickham |
| 5,709,215 A | 1/1998 | Perttu et al. |
| 5,755,738 A | 5/1998 | Kim et al. |
| 5,817,134 A | 10/1998 | Greenhut et al. |
| 5,827,197 A | 10/1998 | Bocek et al. |
| 5,857,977 A | 1/1999 | Caswell et al. |
| 5,891,048 A | 4/1999 | Nigam et al. |
| 5,991,657 A | 11/1999 | Kim |
| 6,029,086 A | 2/2000 | Kim et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Grey |
| 6,148,230 A | 11/2000 | Kenknight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,892,092 B2 | 5/2005 | Palreddy et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,117,035 B2 | 10/2006 | Wagner et al. |
| 7,123,954 B2 * | 10/2006 | Narayan et al. ............... 600/518 |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson |
| 7,302,294 B2 | 11/2007 | Kamath et al. |
| 7,330,757 B2 | 2/2008 | Ostroff et al. |
| 7,346,392 B2 | 3/2008 | Kenknight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |

(56) References Cited

U.S. PATENT DOCUMENTS

| | | |
|---|---|---|
| 2004/0049120 A1* | 3/2004 | Cao et al. .................. 600/521 |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian |
| 2006/0116595 A1 | 6/2006 | Palreddy et al. |
| 2006/0116725 A1 | 6/2006 | Palreddy et al. |
| 2006/0122676 A1 | 6/2006 | Ko et al. |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis et al. |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0015647 A1 | 1/2008 | Palreddy et al. |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2009/0036788 A1 | 2/2009 | Nabutovsky et al. |
| 2009/0043352 A1 | 2/2009 | Brooke et al. |
| 2009/0054796 A1 | 2/2009 | Marcovecchio et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0187227 A1 | 7/2009 | Palreddy et al. |
| 2009/0240157 A1 | 9/2009 | Liam et al. |
| 2009/0240300 A1 | 9/2009 | Liam et al. |
| 2009/0259271 A1 | 10/2009 | Allavatam et al. |
| 2010/0004713 A1 | 1/2010 | Warren et al. |
| 2010/0094369 A1 | 4/2010 | Allavatam et al. |
| 2010/0152798 A1 | 6/2010 | Sanghera et al. |
| 2010/0152799 A1 | 6/2010 | Sanghera et al. |

OTHER PUBLICATIONS

U.S. Appl. No. 12/355,552, filed Jan. 16, 2009; Palreddy et al.

U.S. Appl. No. 61/051,332, filed May 7, 2008; Allavatam et al.

Gunderson et al., "An Algorithm to Predict Implantable Cardioverter-Defibrillator Lead Failure," JACC, Nov. 2004, vol. 44, No. 9, pp. 1898-1902.

Olson et al., "Onset and Stability for Ventricular Tachyarrhythmia Detection in an Implantable Pacer-Cardioverter-Defibrillator," IEEE, (1987) pp. 167-170.

Schuder, "The Role of an Engineering Oriented Medical Research Group in Developing Improved Methods and Devices for Achieving Ventricular Defibrillation: The University of Missouri Experience," PACE, vol. 16, Jan. 1993, pp. 95-124.

Schwake et al., "Komplikationen nit Sonden bei 340 Patienten mit einem Implantierbaren Kardioverter/Defibrillator," Z Kardiol (1999)vol. 88, No. 8 pp. 559-565.

Swerdlow, et al., "Advanced ICD Troubleshooting: Part I," online article at http://www.medscape.com/viewarticle/520588_print, accessed and printed Jul. 7, 2009, indicates publication Jan. 9, 2006 (publication date not confirmed).

Throne, "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.

* cited by examiner

ACCURATE CARDIAC EVENT DETECTION IN AN IMPLANTABLE CARDIAC STIMULUS DEVICE

RELATED APPLICATIONS

The present application claims the benefit of and priority to U.S. Provisional Patent Application No. 61/034,938, filed Mar. 7, 2008 and titled ACCURATE CARDIAC EVENT DETECTION IN AN IMPLANTABLE CARDIAC STIMULUS DEVICE, the disclosure of which is incorporated herein by reference.

The present application is related to U.S. patent application Ser. No. 12/399,914, filed Mar. 6, 2009 and titled METHODS AND DEVICES FOR IDENTIFYING AND CORRECTING OVERDETECTION OF CARDIAC EVENTS, published as US Patent Application Publication Number 2009-0259271, now U.S. Pat. No. 8,160,686, which claims the benefit of and priority to US Provisional Patent Application No. 61/051,332, filed May 7, 2008, and the disclosures of which are also incorporated herein by reference.

FIELD

The present invention relates generally to implantable medical device systems that sense and analyze cardiac signals. More particularly, the present invention relates to implantable medical devices that capture cardiac signals within a patient's body in order to classify cardiac activity and direct therapy for treatment of arrhythmias.

BACKGROUND

Implantable cardiac stimulus devices typically sense cardiac electrical signals within a patient in order to classify the patient's cardiac rhythm as normal/benign or malignant in order to prevent, treat, or terminate malignant rhythms. Such malignant rhythms can include, for example, ventricular fibrillation and some ventricular tachycardias. How accurately an implantable medical device analyzes captured signals determines how appropriately it can direct therapy.

New and alternative methods and devices for detection and/or analysis of captured cardiac events in implantable medical devices are needed.

SUMMARY

Various illustrative embodiments of the present invention are directed toward improving accuracy of cardiac event detection by implantable medical devices. The invention may be embodied in methods and/or devices.

DETAILED DESCRIPTION

Figure 1:
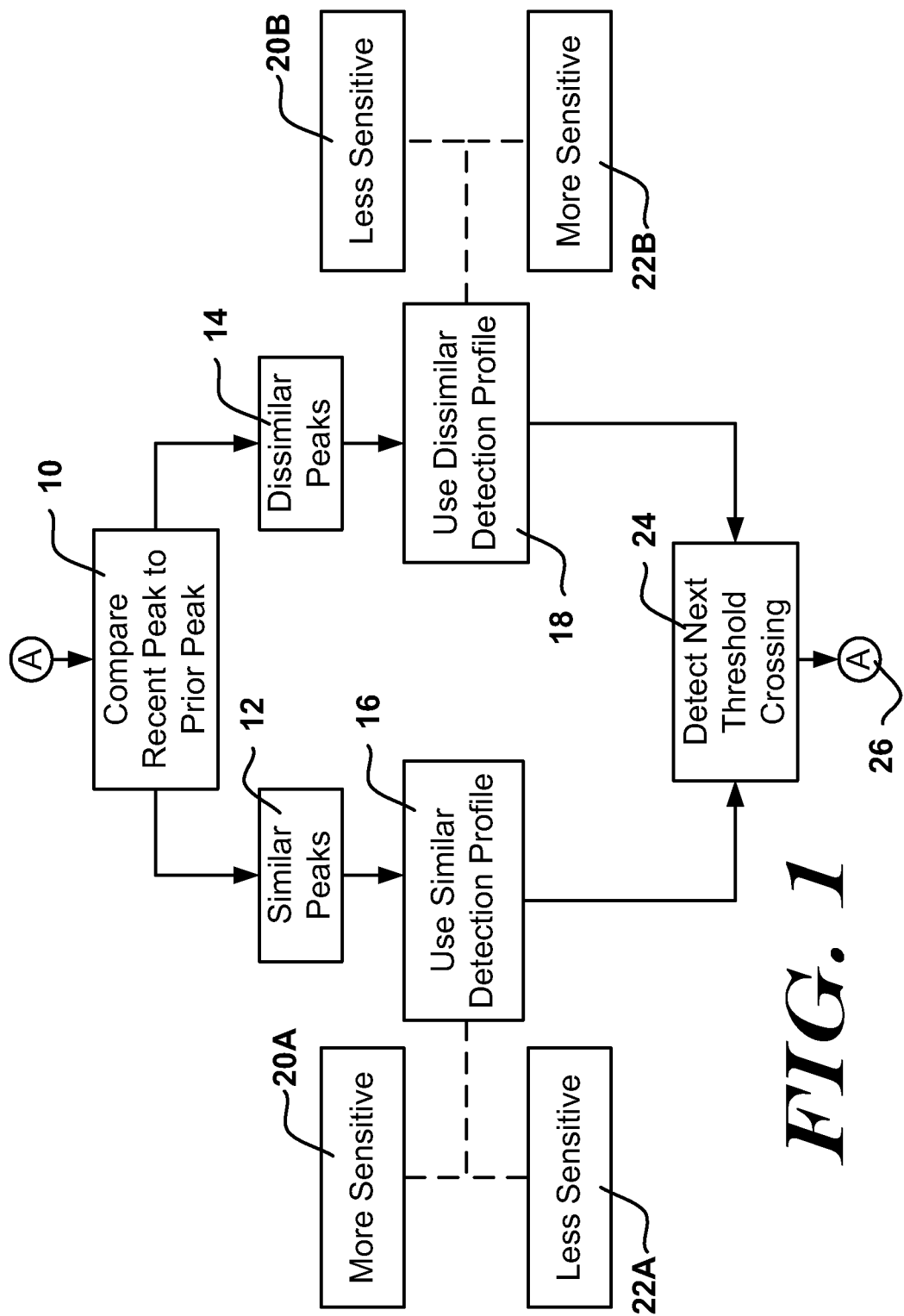
FIG. 1 is a flow diagram showing a method for detection including identifying and responding to amplitude similarity/dissimilarity of detected events.

The following detailed description should be read with reference to the drawings. The drawings, which are not necessarily to scale, depict illustrative embodiments and are not intended to limit the scope of the invention.

Unless implicitly required or explicitly stated, the methods below do not require any particular order of steps. It should be understood that when the following examples refer to a "current event," in some embodiments, this means that the most recently detected event is being analyzed. However, this need not be the case, and some embodiments perform analysis that is delayed by one or more event detections or a fixed period of time.

Implantable devices typically calculate a heart rate or beat rate for the implantee. Heart or beat rate is typically given in beats-per-minute (bpm). Such devices then use the heart rate either alone or in conjunction with some other factor (sometimes morphology is used, for example) to determine whether the implantee needs therapy.

The calculation of heart rate can be performed by observing the rate at which "events" are detected by the implanted device. In an illustrative example, an event is detected by comparing received signals to a detection threshold, which is defined by a detection profile. Illustrative examples of detection profiles are shown in FIGS. 3, 6A, 6B and 11-12. A detected event is declared when the received signal crosses the detection threshold.

A cardiac electrogram includes several portions (often referenced as "waves") that, according to well known convention, are labeled with letters including P, Q, R, S, and T, each of which corresponds to particular physiological events. It is typical to design detection algorithms to sense the R-wave, though any portion, if repeatedly detected, can be used to generate a beat rate. If morphology (shape) analysis is used in addition to heart rate, the system may capture and/or analyze the portion of the cycle that includes the Q, R and S waves, referred to as the QRS complex. Other portions of the patient's cardiac cycle, such as the P-wave and T-wave, are often treated as artifacts that are not sought for the purpose of estimating heart rate, though this need not be the case.

Sensing may be performed in the near field or far field. Intracardiac electrograms are dominated by signal components generated in the near field, while surface or subcutaneous sensing captures signals in the far field. The R-wave often has larger amplitude than other portions of the cardiac cycle, though this can vary depending upon how and from what location the signal is sensed and/or with patient physiology.

Typically, for purposes of ascertaining rate each cardiac cycle is counted only once. Overdetection (such as a double or triple detection) may occur if the device declares more than one detected event within a single cardiac cycle. This may happen if an R-wave and a trailing T-wave are both detected from a single cardiac cycle or if a wide QRS complex is detected twice. Overdetection may also occur if noise causes an event to be declared when no cardiac event has taken place, for example, due to external noise, pacing artifact, skeletal muscle noise, electro-therapy, etc.

Overdetection can lead to overcounting of cardiac cycles. For example, if one cardiac cycle takes place and a detection algorithm declares multiple detected events, overdetection has occurred. If the heart rate is then calculated by counting each of these detections, overcounting occurs.

Calculated heart rates may be used alone or in combination with other factors to classify cardiac activity as malignant or benign. Therapy decisions are usually made based upon such classification. Overcounting in reliance on overdetected events can result in erroneously high rate calculation. Miscalculation of heart rate can lead to incorrect therapy decisions and, particularly, incorrect therapy delivery. However, simply preventing overdetection by rendering a device insensitive to received signals can cause undersensing, which may impair or delay delivery of needed therapy.

An illustrative embodiment makes use of a detection method as shown in the high-level functional block diagram of FIG. 1. The method is briefly introduced here, with more detailed examples provided below. The illustrative method makes use of a detection profile as shown in one of FIGS. 3, 6A, 6B, 11 and/or 12. In the illustrative example of FIG. 1, when detected events are similar to one another, a relatively more sensitive detection profile is used, and when detected events are dissimilar from one another, a relatively less sensitive detection profile is used.

As shown at step 10, a peak for a recent detected event is compared to a prior peak. The illustrative example uses the comparison at 10 to categorize the recent detected event peak as either similar 12 or dissimilar 14 relative to the prior peak. The comparison at 10 may take the following form, for example:

$$A \leq \frac{\text{New Peak Amplitude}}{\text{Prior Peak Amplitude}} \leq B$$

where A and B are predetermined values. In the illustrative example, if the above formula yields a "True" outcome, then the peaks are similar; otherwise, they are dissimilar.

The quotient in the middle of this formula is referred to as the peak ratio. In an illustrative example, A=0.8 and B=1.2. In other examples, A may be in the range of 0.5-0.9, and B may be in the range of 1.1-1.5. Additional examples of similar/dissimilar analysis are provided below.

If the recent detected event peak is similar to the prior peak, as shown at 12, a "Similar" detection profile is applied, as shown at 16. On the other hand, if the recent detected event peak is dissimilar from the prior peak, as shown at 14, a "Dissimilar" detection profile is applied, as shown at 18. The selection of the Similar or Dissimilar detection profile modifies the sensitivity of the detection method. In one example, the Similar Detection profile is more sensitive than the Dissimilar Detection profile as shown at 20A/20B. In another example, the Similar Detection profile is less sensitive than the Dissimilar Detection profile, as shown at 22A/22B.

The adopted Similar or Dissimilar detection profile 16, 18 is then used to detect the next detection profile threshold crossing, as shown at 24. The method then iterates through A 26.

Examples where a detection profile is more or less sensitive are shown below. In short, a detection profile typically defines amplitudes at given points in time, and if the captured signal exceeds the detection profile defined amplitude, a detection occurs. By raising or lowering the detection profile and/or modifying the timeline of the detection profile, sensitivity is raised or lowered.

In another embodiment, the similar/dissimilar analysis may include an interval rule. For example, the likelihood of double detection decreases when the interval between two detections is long. In an illustrative embodiment, two consecutive detections separated by a relatively long interval (greater than, for example, 500 milliseconds) are not subject to the similar/dissimilar analysis, as they are likely not overdetected during the long interval. Instead, when an interval of a length greater than a predetermined threshold is identified, one or the other of the similar or dissimilar detection profile is adopted automatically.

Figure 2:
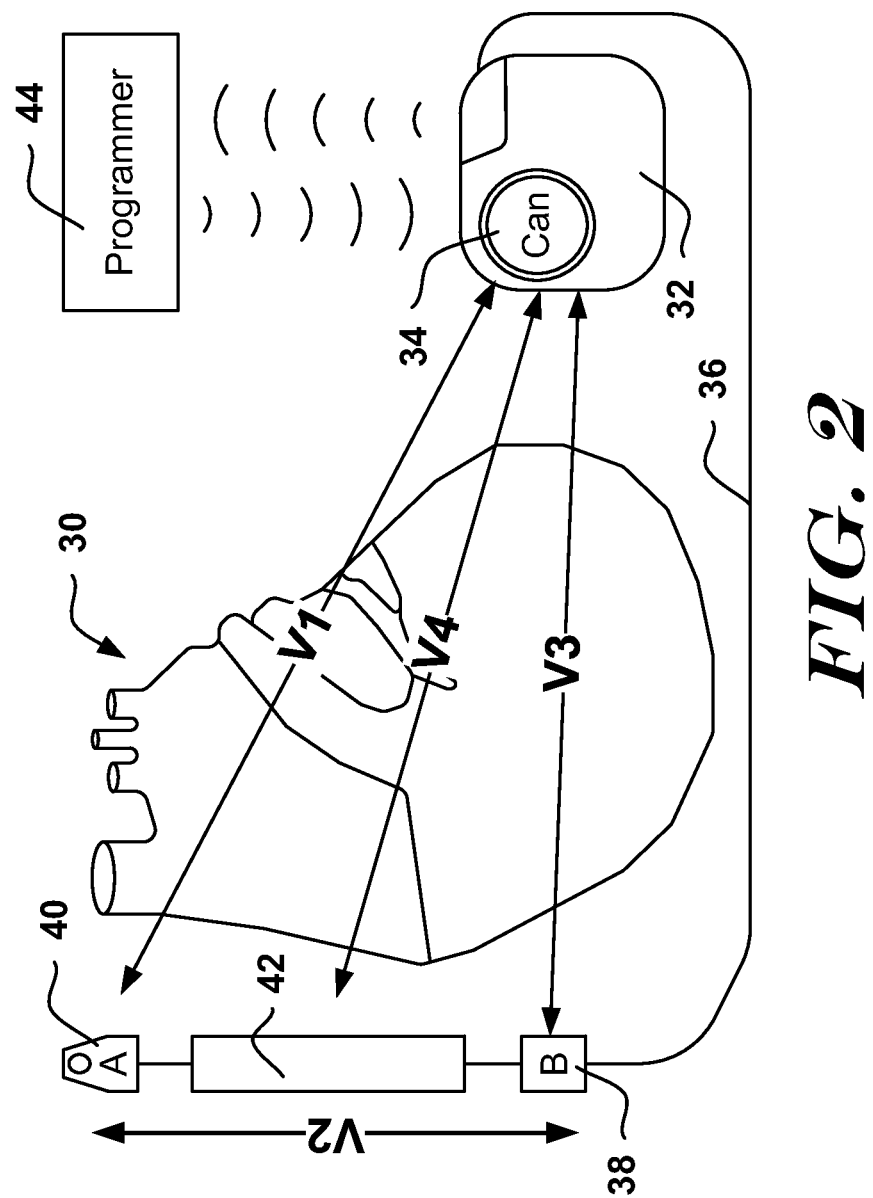
FIG. 2 illustrates a representative subcutaneous implantable cardiac stimulus system.

It is contemplated that the present invention may be embodied in several forms including at least implantable cardiac monitoring systems and implantable cardiac stimulus systems. An illustrative subcutaneous cardiac stimulus system is shown in FIG. 2. The subcutaneous system is shown relative to a heart 30, and includes a canister 32 coupled to a lead 36. The canister 32 houses operational circuitry for performing analysis of cardiac activity and for providing a stimulus output. A can electrode 34 is disposed on the canister 32. In some embodiments, rather than a discrete electrode 34, a surface of the canister 32 may serve as an electrode.

The lead 36 includes three illustrative electrodes shown as ring electrode 38, coil electrode 42, and tip electrode 40. These electrodes 38, 40, 42 and the can electrode 34 may define a plurality of sensing vectors, such as V1, V2, V3 and, optionally, V4. If desired, one or more vectors V1, V2, V3, and V4 may be chosen for use as a default sensing vector, for example, as discussed in US Patent Application Publication Number 2007-0276445 titled SYSTEMS AND METHODS FOR SENSING VECTOR SELECTION IN AN IMPLANTABLE MEDICAL DEVICE. Illustrative subcutaneous systems are also shown in U.S. Pat. Nos. 6,647,292, 6,721,597 and 7,149,575. Stimulus may be applied using any chosen pair of electrodes; one illustrative example uses the can electrode 34 and the coil electrode 42 to deliver stimulus. In yet another embodiment, multiple sensing vectors may be used simultaneously.

A programmer 44 is also shown. The programmer can be used to configure the implant system as desired through methods that are widely known. These may include, for example, radiofrequency or inductive telemetry communication.

The present invention is not limited to any particular hardware, implant location or configuration. Instead, it is intended as an improvement upon any implantable cardiac monitoring and/or treatment system. Embodiments of the present invention may take the form of devices or systems for use as subcutaneous-only, transvenous single or multi-chamber, epicardial or intravascular implantable defibrillator or monitoring systems, or as methods of use in any such system.

FIG. 2 omits various anatomical landmarks. The illustrative system shown would be implanted outside of the ribcage (not shown) of the implantee. The location illustratively shown places the canister 32 at approximately the left axilla of the implantee, level with the cardiac apex, with the lead 36 extending medially toward the sternum and then toward the head of the patient along the left side of the sternum. For example, the implant may be similar to that shown in commonly assigned US Patent Application Publication Number 2006-0122676 titled APPARATUS AND METHOD FOR SUBCUTANEOUS ELECTRODE INSERTION, now U.S. Pat. No. 7,655,014.

The canister 32 may be placed in anterior, lateral, and/or posterior positions including, without limitation, axillary, pectoral, and sub-pectoral positions, as well as placements on either the left or right side of the patient's torso. The lead 36 may then be placed in any of a number of suitable configurations including anterior-posterior combinations, anterior-only combinations, transvenous placement, or other vascular placements. An embodiment of a monitoring system may be a subcutaneously implanted system having a housing with multiple electrodes thereon, with or without a lead.

Figure 3:
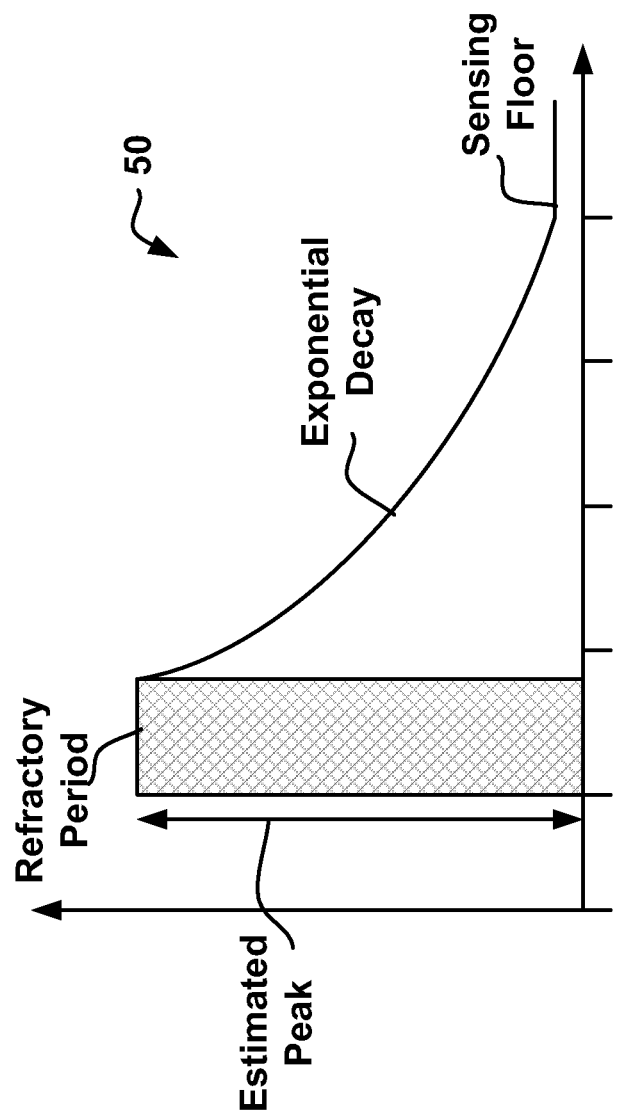
FIG. 3 illustrates a prior art detection profile.
Figure 4:
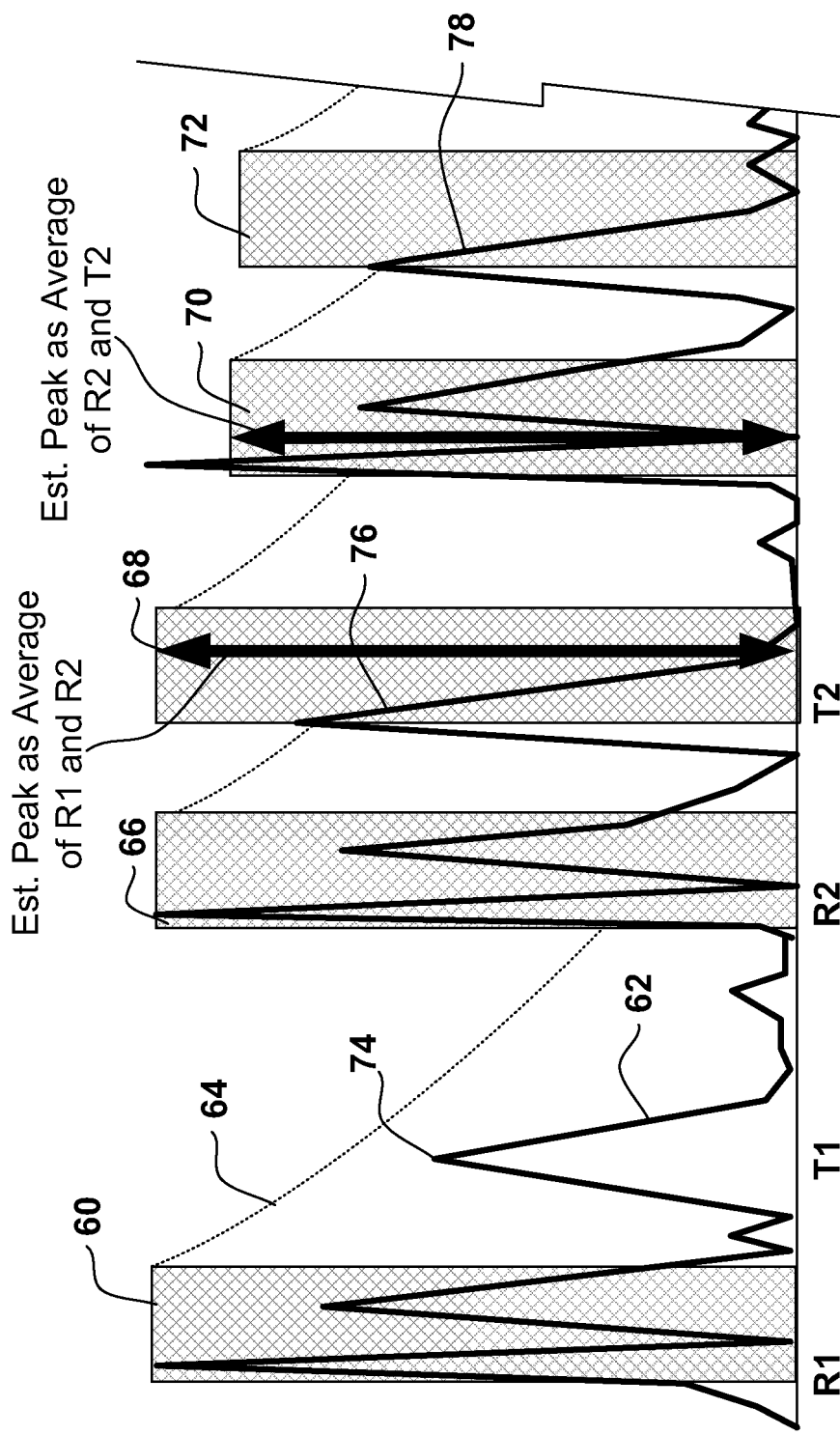
FIG. 4 graphically depicts overdetection of a captured cardiac signal.
Figure 5:
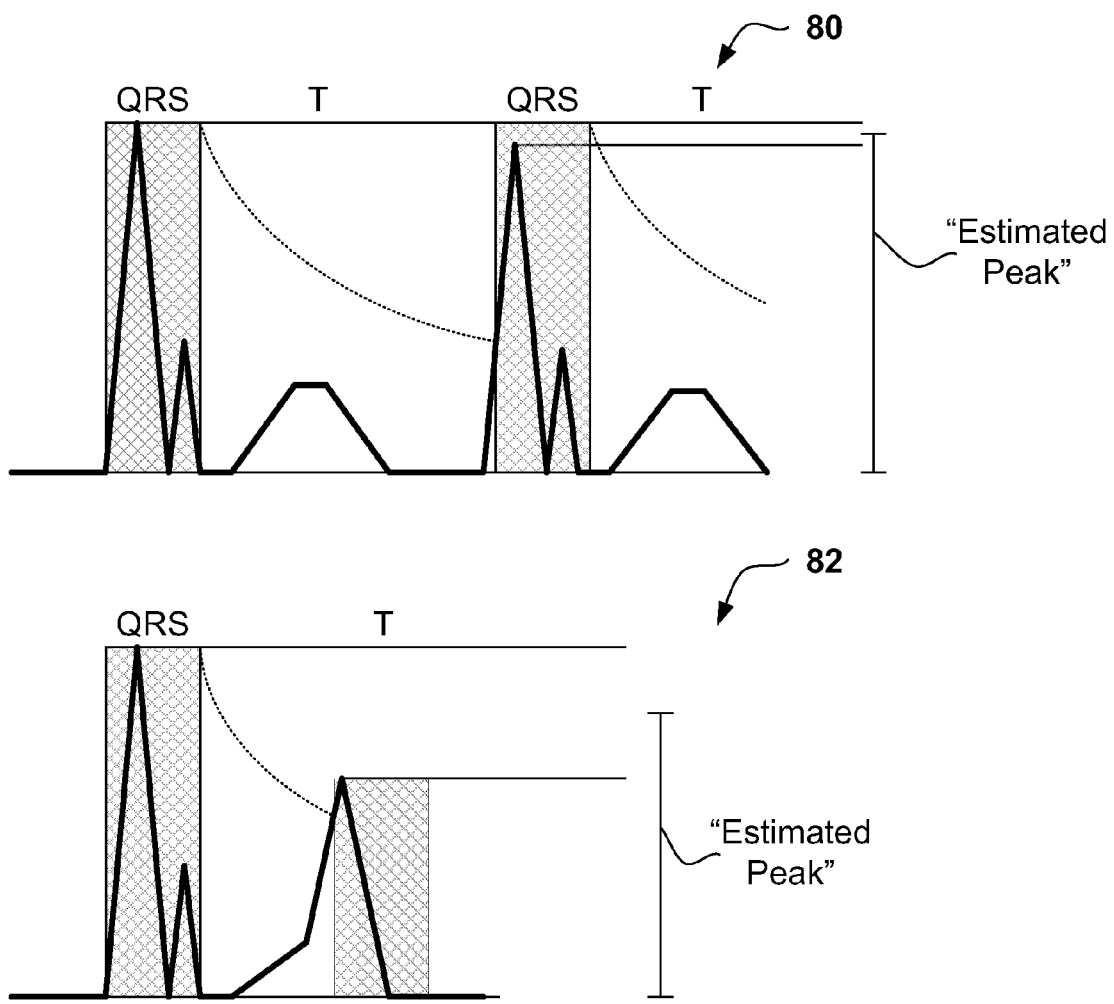
FIG. 5 illustrates calculation of "estimated peak" using an average of two prior peaks.

FIGS. 3-5 provide an introduction to a detection profile and its use. The application of the detection profile of FIG. 3 to a captured cardiac signal is shown in FIG. 4, which illustrates overdetection using such a profile. FIG. 5 illustrates calculation of "estimated peak" that is used to generate amplitudes defined by a detection profile as shown in FIGS. 3-4. It should be noted that, for purposes of simplicity, the detection profiles shown herein are illustrated using a rectified signal. Those of skill in the art will recognize that the detection profile for an unrectified signal would effectively define the detection profile on the negative side of the sensing baseline as well.

FIG. 3 illustrates a detection profile at 50, with portions thereof labeled for illustrative purposes. The detection profile includes a refractory period, shown in cross-hatching. The refractory period is an initial time period that follows a threshold crossing. During the refractory period, captured signal data may be recorded and/or analyzed, but additional detected events are not declared. Following the refractory period is an exponential decay period, as shown. The exponential decay brings the detection threshold down, over time, from a starting point to the sensing floor of the device. Some challenges with this detection profile are discussed by U.S. Pat. No. 5,709,215 to Perttu et al.

The "sensing floor" may be defined by the hardware limits of the device and/or by the ambient noise environment of the device. A sensing floor may also be selected in any suitable manner. Values for the sensing floor may vary depending upon the characteristics of the particular implantable cardiac stimulus system including, for example, input circuitry, filter capability, electrode location and size, and patient physiology.

As used herein, and for illustration purposes, the height shown for the detection profile during each refractory period represents the "estimated peak" amplitude of the cardiac signal at that time. In operation, the implanted device makes use of one or more prior detected events to estimate the amplitude of peaks in the cardiac signal. Illustrative calculations of estimated peak are shown in FIG. 5. In the illustrative detection profile of FIG. 3, the exponential decay following the refractory period uses the estimated peak as its starting point, and follows an exponential decay curve from the estimated peak to the sensing floor or some other selected value.

FIG. 4 illustrates a problem that may arise during application of the detection threshold of FIG. 3, which is shown at 64, to a captured cardiac signal 62. In FIG. 4, refractory periods are indicated by cross-hatching, as shown at 60, 66, 68, 70 and 72. Refractory periods at 60, 66 and 70 cover QRS complexes in the captured signal 62; these detections can be considered "accurate," as the desired portion of the cardiac signal has been detected.

T-waves are shown at 74, 76 and 78. As can be seen at 74, the T-wave following refractory period 60 does not cause a detection, although it is close in amplitude to the decaying detection profile 64. The next T-wave, at 76, crosses the decaying detection profile, resulting in a detection followed by refractory period 68. The detection of the T-wave 76 creates two potential problems. First, an overdetection occurs, since two detections (resulting in refractory periods 66, 68) occur in a single cardiac cycle. Second, the T-wave 76 has a different amplitude than the R-waves of the captured signal and can therefore affect the calculation of estimated peak, as shown by FIG. 5.

Referring to FIG. 5, the illustrative example uses the average amplitude of two prior peaks as the "estimated peak." As shown at 80, correct identification of QRS complexes enables a calculation of estimated peak that is an average of the R-wave amplitude for the previous two QRS complexes. As shown at 82, however, detection of the T-wave as the second peak causes a calculation of estimated peak that may be lower than the R-wave peak.

Returning to FIG. 4, the estimated peak shown at 68 is an average of the amplitudes for R-waves R1 and R2, however, the estimated peak shown at 70 is an average of the amplitudes for R-wave R2 and T-wave T2. Since the T-waves are lower in amplitude than the R-waves, as shown at 70, the estimated peak following T-wave 76 is lowered, increasing the likelihood that another T-wave will also cause a threshold crossing and detection. In the illustrative example, T-wave 78 crosses the detection threshold, causing the system to again declare a detected event. Thus T-wave 76 contributes to the overdetection of T-wave 78, and the overdetection of T-waves becomes a self-perpetuating condition.

Figure 6A:
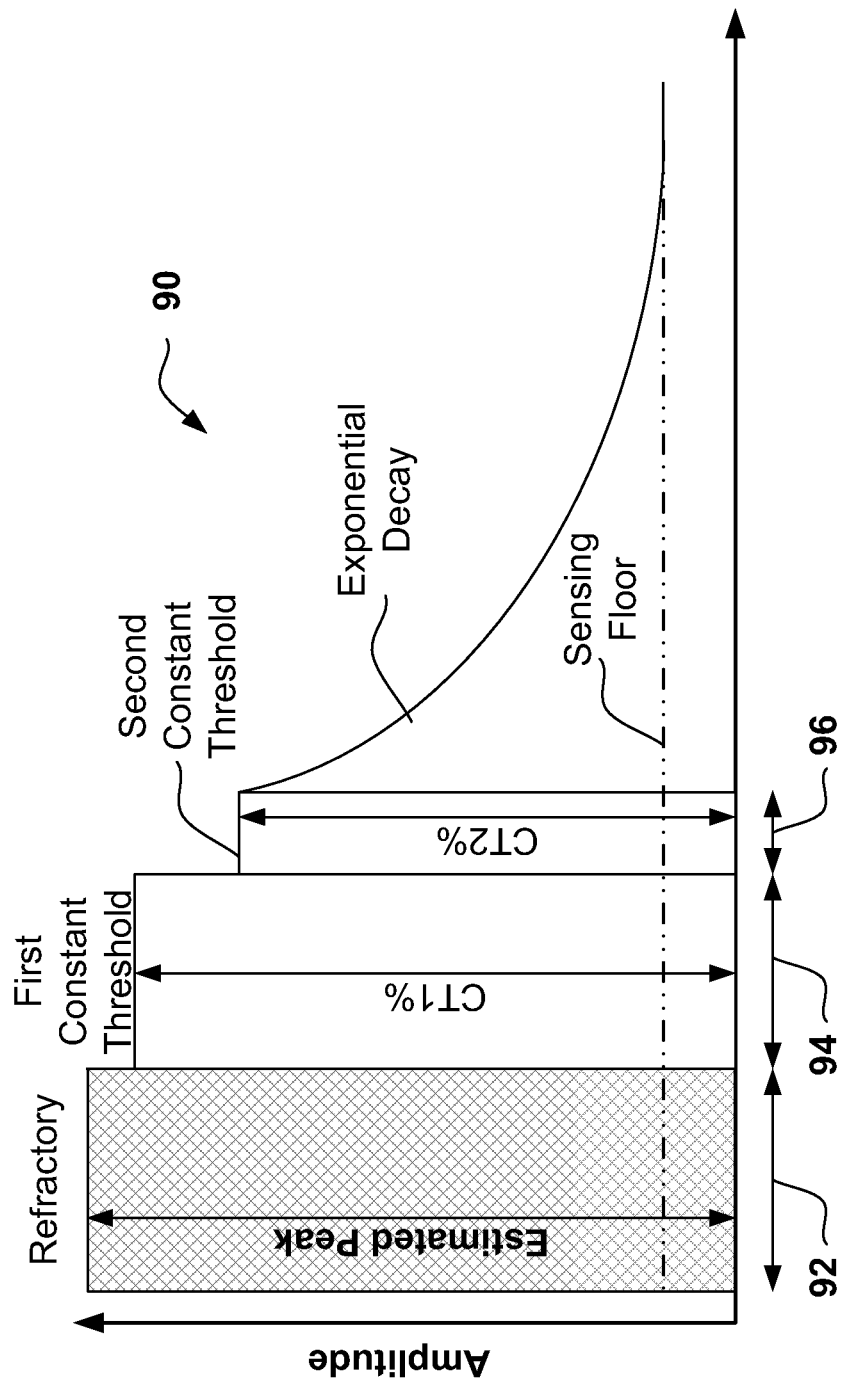
FIGS. 6A-6B show illustrative detection profiles.
Figure 6B:
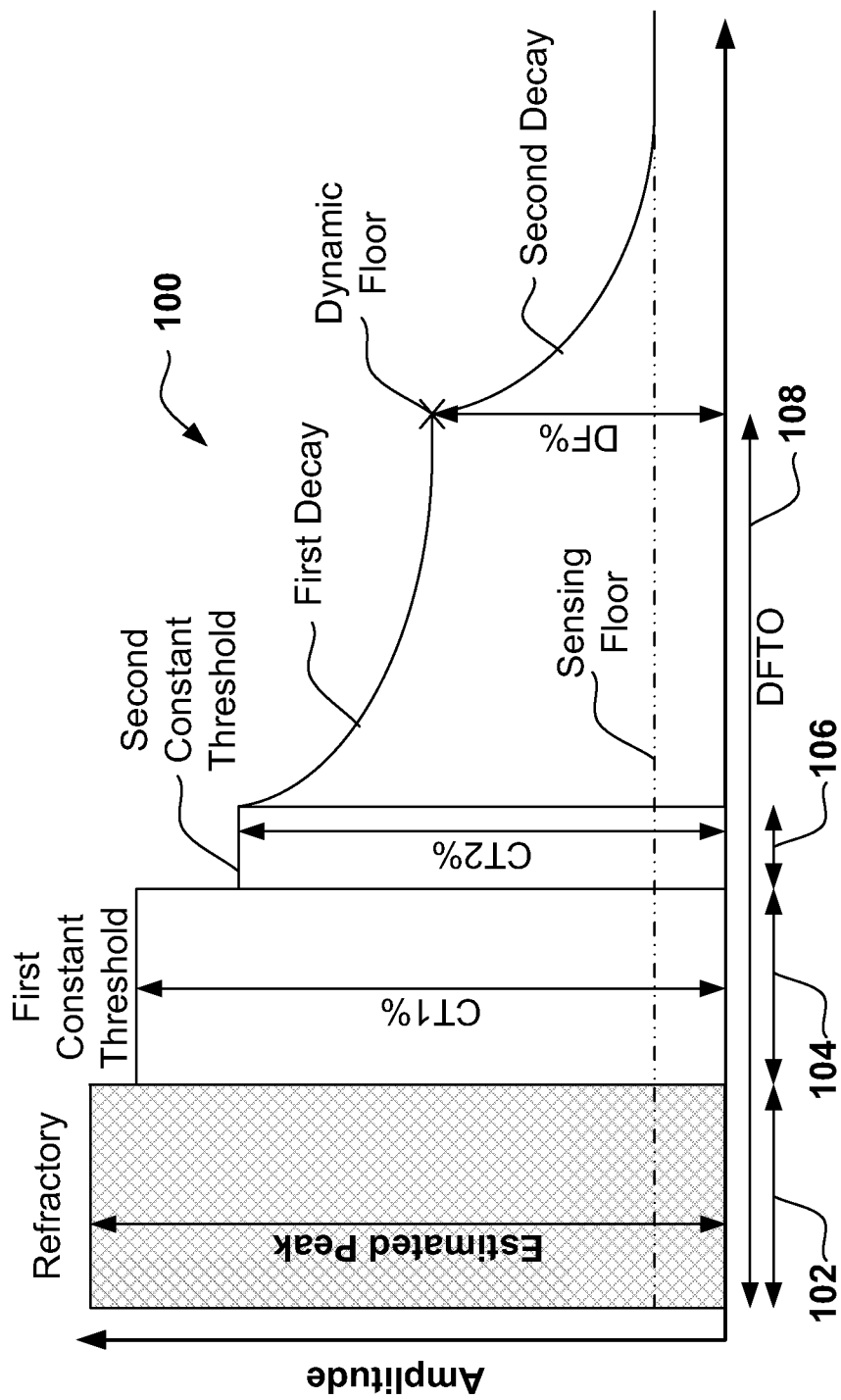

FIGS. 6A-6B show illustrative detection profiles that can be manipulated in accordance with some examples of the present invention. Referring to FIG. 6A, a detection profile is shown at 90 and includes a refractory segment having a refractory duration 92, which is immediately followed by a first constant threshold segment (CT1) using a CT1 % of the estimated peak for its amplitude and a CT1 duration 94. Following CT1 is a second constant threshold segment (CT2) using a CT2 % of the estimated peak for its amplitude and CT2 duration 96. Following CT2 is an exponential decay which begins at amplitude CT2 % of the estimated peak and decays toward the sensing floor.

For the illustrative example of FIG. 6A, at least the following variables may be manipulated to change the sensitivity of the detection profile:

Durations 92, 94, or 96;
Amplitudes CT1 %, CT2 % of the estimated peak;
The start point of the Exponential Decay; and/or
The time constant of decay for the Exponential Decay.

In illustrative examples, these variables are manipulated singly or in combination to increase or decrease sensitivity in response to identified similarity or dissimilarity between detected event peak amplitudes. For example, extending any of the durations 92, 94, 96 reduces the sensitivity of the overall detection profile. In some embodiments, the refractory period 92 remains fixed, while combinations of the other variables are modified.

FIG. 6B illustrates another detection profile 100. FIG. 6B incorporates a "dynamic floor." The dynamic floor is a detection profile component that is set to a selected value above the sensing floor and used as an intermediate "floor" for the detection profile. An illustrative dynamic floor is invoked until a dynamic floor time-out (DFTO), at which time the detection profile begins decaying toward the sensing floor.

Referring again to FIG. 6B, a detection profile 100 includes a refractory segment having a refractory duration 102, which is followed by a first constant threshold segment (CT1) using CT1 % of the estimated peak as its amplitude and having a CT1 duration 104. After CT1 is a second constant threshold segment (CT2) using CT2 % of the estimated peak as amplitude, and having a CT2 duration 106. Next is a first decay period, which starts from the amplitude of CT2 % and ends at a dynamic floor having an amplitude DF %, with each of CT2 % and DF % based on the estimated peak. The DFTO 108 is used to define the duration of the first decay. Following the first decay is a second decay to the sensing floor. The first and second decays may use the same time constant of decay, or may use different time constants of decay.

For the example shown in FIG. 6B, the inclusion of the dynamic floor and a DFTO 108 provides two additional variables that can be modified in response to identified similarity/dissimilarity. While not shown, in yet another embodiment, CT2 may be omitted such that the first decay starts from CT1 %, or some other predetermined percentage of estimated peak, or even from a constant not associated with the estimated peak. In another example, CT2 is used as a placeholder for the start of the first decay period and is given a very short duration equal to a single sample period. While exponential decays are shown in FIGS. 6A-6B, any suitable decay shape may be used, for example, including constant ramp decays or other non-exponential functions, for example.

Figure 7A:
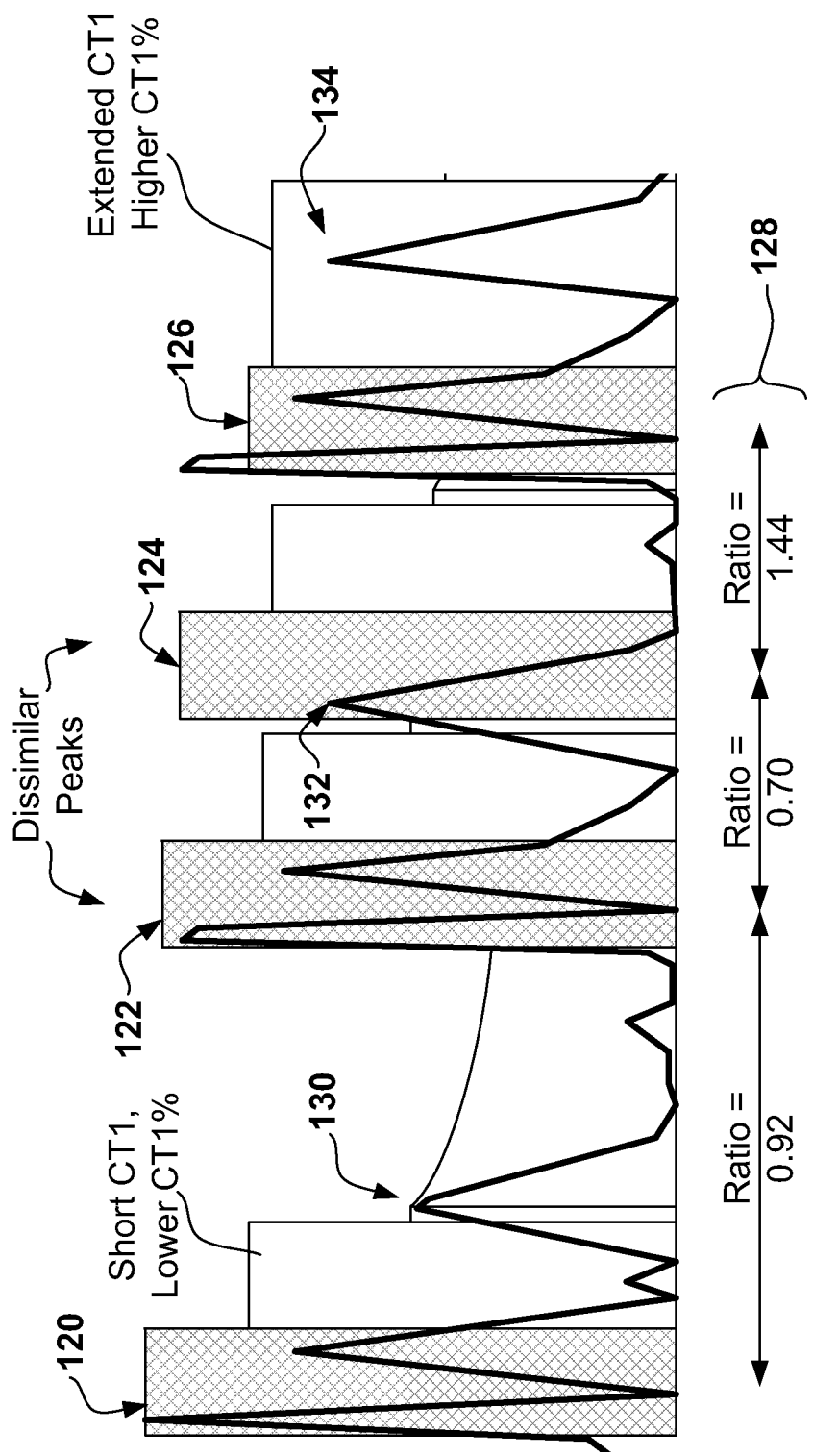
FIGS. 7A-7B graphically show changes in dynamic detection profiles based on similarity/dissimilarity measures of captured signals.
Figure 7B:
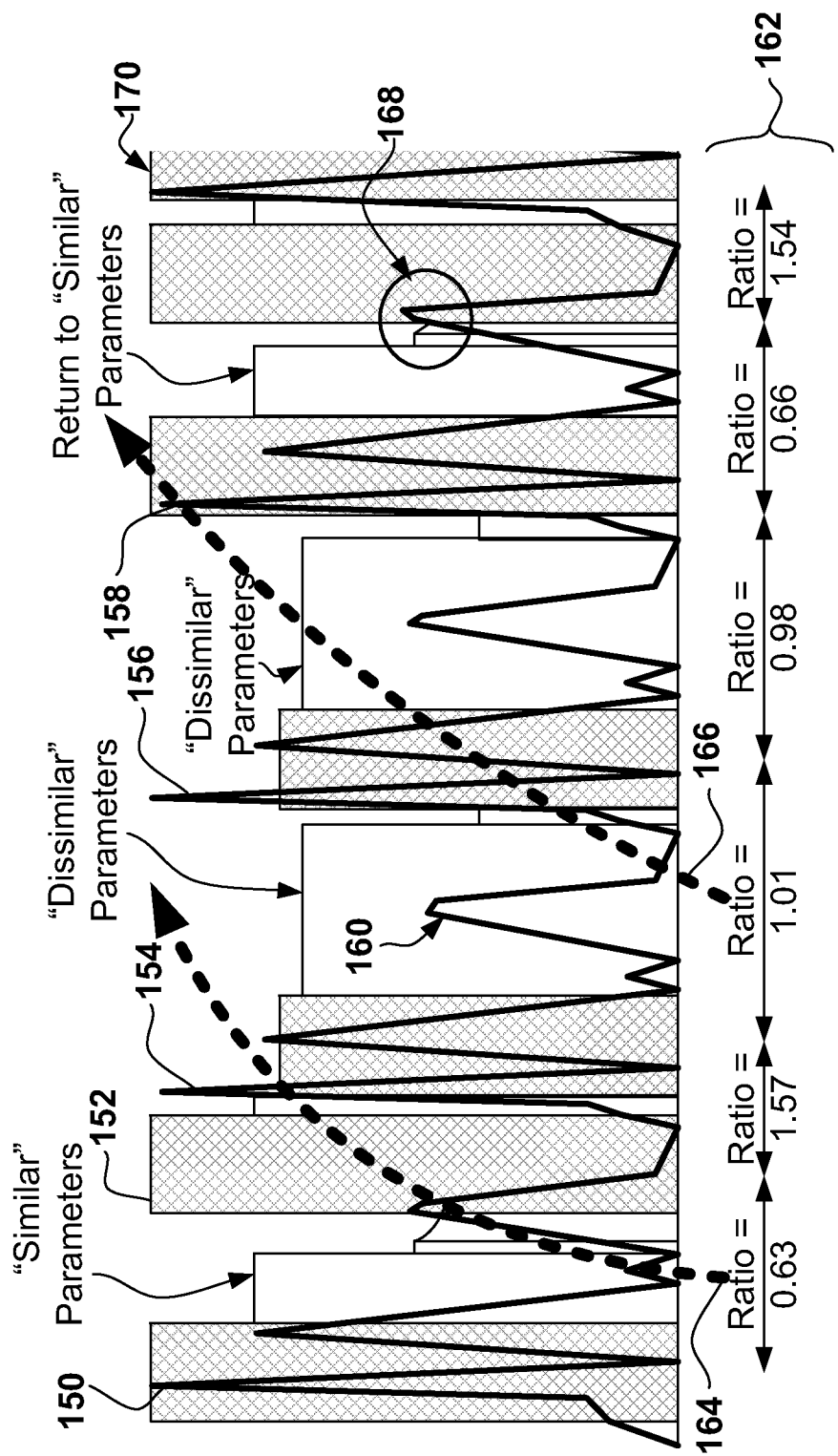

FIGS. 7A-7B show illustrative adaptive profiles and a system-level response to changes in peak amplitudes. In FIG. 7A, a first detection is shown at 120. The detection profile is shown in a form generally corresponding to that of FIG. 6B, though a detection profile as in FIG. 6A could also be used. Additional detections occur at 122, 124 and 126.

In the illustrative example of FIG. 7A, immediately prior to detection 120, there were consecutive similar peaks (not shown). This leads to the inclusion of a relatively short CT1 and low CT1 %, as indicated. With these parameters, as shown at 130, a T-wave nearly creates a detection threshold crossing.

The illustrative system keeps track of the peak amplitude during the refractory periods (again shown as cross-hatched blocks). The peak values are shown beneath the refractory periods in analog-to-digital conversion (ADC) units. ADC units represent the output of analog-to-digital conversion within the device; in the Figures these units are shown merely to help illustrate other concepts.

The peak values are used to calculate peak ratios shown at 128. The peak ratio for detections 120 and 122 is 0.92. In this illustrative example, peak ratios of about 0.8-1.2 are defined as indicating "similar" peaks, so detections 120 and 122 are considered similar. Other ranges defining similar/dissimilar peak ratios, and other measures of similar/dissimilar may be used.

The detection profile following detection 122 is similar to the detection profile following detection 120 because the prior peak amplitude for detection 120 is similar to that of the immediately preceding peak amplitude (the preceding peak is not shown). T-wave 132 following detection 122 causes an overdetection 124. The peak for T-wave 132 is lower than the R-wave peak for detection 122. These peaks yield a peak ratio of 0.70, which falls outside of the range that defines "similar" peak ratios for the example (0.8-1.2 being considered "similar").

The system as shown has a built-in delay of one event, so detection following the overdetection 124 uses the "similar" detection profile. However, in contrast to events 120, 122 and 124, the detected event at 126 is followed by a detection profile based on "dissimilar" detection profile parameters. This results in modifications, as indicated, including extended CT1 duration and a higher CT1 %. As a result, the T-wave shown at 134 does not cause a detection threshold crossing and no detected event is declared for T-wave 134. The modification in view of the dissimilar peak amplitudes prevents continued overdetection in the illustrative example shown in FIG. 7A.

In an illustrative example, FIG. 7A makes use of the following detection profile parameters (% indicates percent of the estimated peak):

|  | Dissimilar | Similar |
| --- | --- | --- |
| Refractory: | 200 ms | 200 ms |
| CT1 %: | 95% | 80% |
| CT1 Duration: | 350 ms | 200 ms |
| CT2 %: | 50% | 50% |
| CT2 Duration: | 4 ms | 4 ms |
| DF %: | 50% | 37.5% |
| DETO: | 720 ms from the start of Refractory | |

The inclusion of DF % and DF TO is not apparent from FIG. 7A and, if desired, these may be omitted in some embodiments. The time constants for decay may be any suitable value. In an illustrative example, the time constant of decay for the above parameters is in the range of 400 milliseconds. Additional variations of and ranges for these parameters are provided below.

FIG. 7B shows the analysis as it continues, with more detected events shown. Starting at the left, detected event 150 is associated with a detection profile using a "similar" detection profile configuration. This results in overdetection of the trailing T-wave, shown at detection 152. As shown following the next detection, at 154, detection 152 of a T-wave results in reduction of the estimated peak (again, the estimated peak is shown as the height of the cross-hatched block that represents the refractory period).

However, the overdetection 152, considered relative to peak 150, results in calculation of a peak ratio of 0.63 (peak ratios are shown at 162). As indicated by the line/arrow 164, a low peak ratio causes the use of a "dissimilar" detection profile configuration following the detection at 154. The delay in this illustrative example is based on a hardware environment in which the peak associated with a given refractory period is not read as a peak until after the end of the given refractory period. It is contemplated that in some hardware environments, the peak and peak ratio could be found in real-time, such that a one beat delay is avoided. In such an example, a "dissimilar" configuration could be invoked during or following the refractory period of detection 152.

Once the "dissimilar" configuration is invoked following detection 154, the detection profile successfully passes over the next T-wave 160. The next detection, shown at 156, is again an accurate detection caused by an R-wave. Because the T-wave detection at 152 is dissimilar in height from the detection at 154 (as well as 150), the peak ratio of 1.57 causes the continued use of the "dissimilar" configuration following detection 156. Again, the detection profile successfully passes over a T-wave. Detection 158 follows. As indicated by the line/arrow 166, the similarity of the peaks for detections 154 and 156 (peak ratio of 1.01) causes the resumption of the more sensitive "similar" configuration.

As shown at 168, the T-wave following detection 158 is detected. The "dissimilar" detection profile configuration will be invoked again. As shown in this illustrative example, during time periods in which overdetection is avoided, similar peaks occur and the more sensitive detection profile configuration associated with similar peaks is invoked. Thus a cycle can develop in which the device transitions between dissimilar and similar detection profile configurations.

The illustrative detection pattern results in sets of four detections in which three R-waves and one overdetected T-wave appear. If the actual heart rate is 100 bpm, consistent overdetection of every T-wave (for example, as shown in FIG. 4) would yield a calculated rate of 200 bpm. A beat rate of 200 bpm may be considered tachyarrhythmic for a substantial number of patients who are candidates for ICD implantation and may create a risk of inappropriate therapy. The example of FIG. 7B, however, would calculate a rate of about 133 bpm, which is unlikely to cause inappropriate therapy.

If desired, a counter or other hysteresis tool may be used to slow the cycling between "similar" and "dissimilar" detection profile configurations. In an illustrative example, once invoked, a detection profile configuration would be used for some predetermined number of detections before invoking a different detection profile configuration. For example, at least 5 detections would occur using a detection profile configuration before a different one could be called. In another example, the hysteresis could be "one-sided," that is, hysteresis could apply only when one of the "similar" or "dissimilar" configurations is invoked. In the example of FIG. 7B, no added hysteresis is provided to avoid delayed identification of malignant fast arrhythmias such as ventricular fibrillation.

Figure 8:
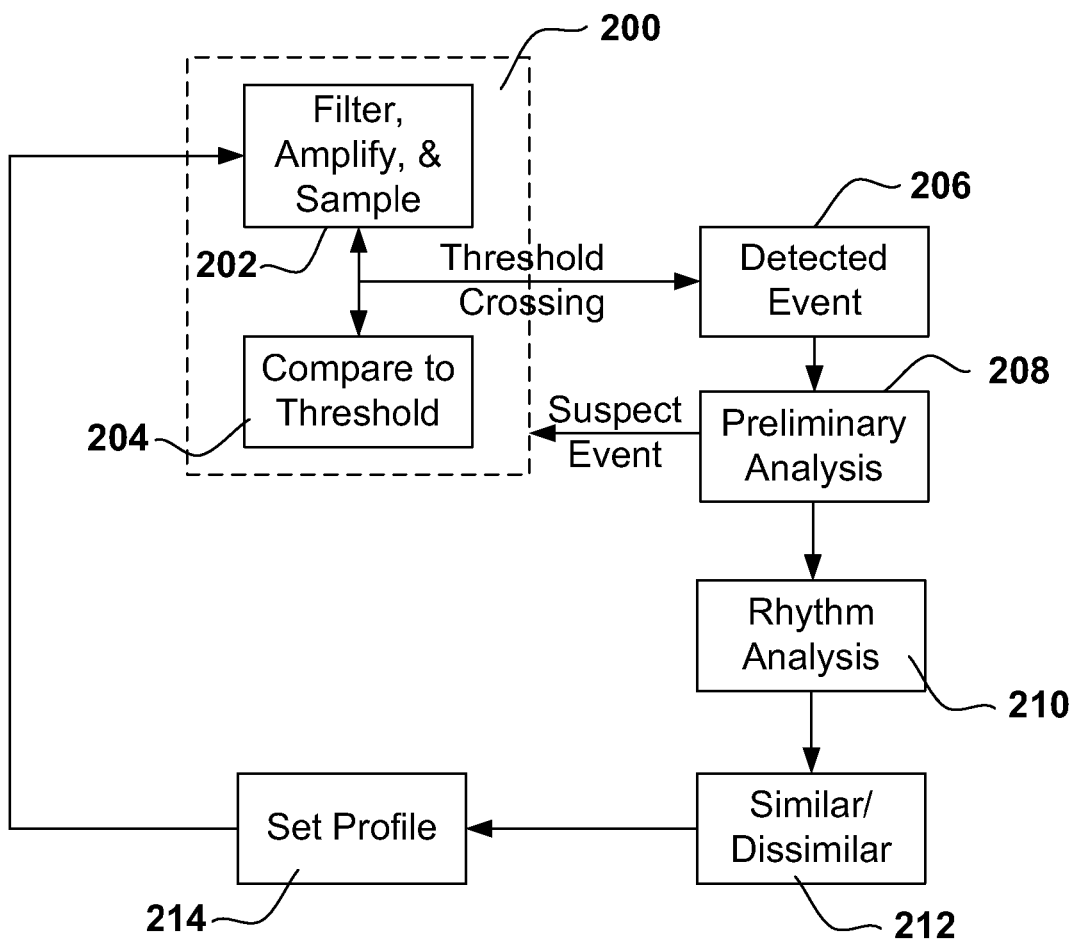
FIG. 8 is a flow diagram of an illustrative example of cardiac signal analysis in an implantable medical device.

FIG. 8 is a flow diagram of an illustrative example of cardiac signal analysis in an implantable medical device. The illustrative example of FIG. 8 includes a detection loop shown at 200, in which incoming signal is filtered, amplified and sampled, as shown at 202. The signal may be rectified in block 202, if desired.

The samples are then compared to a threshold defined by a detection profile as indicated at step 204. Once a threshold crossing occurs, the detection loop 200 is exited and a detected event is declared as shown at 206. If morphology analysis is used, when the detected event is declared 206, various steps may be taken to define a sample window associated with the detected event, for example, as discussed in commonly assigned US Patent Application Publication Number 2006-0116595, now U.S. Pat. No. 7,376,458 and titled METHOD FOR DEFINING SIGNAL TEMPLATES IN IMPLANTABLE CARDIAC DEVICES; and/or commonly assigned US Patent Application Publication Number 2006-0116725, now U.S. Pat. No. 7,477,935 and titled METHOD AND APPARATUS FOR BEAT ALIGNMENT AND COMPARISON.

Next, preliminary analysis is performed, as indicated at 208. This may include, for example, waveform appraisal discussed in commonly assigned U.S. Pat. No. 7,248,921, titled METHOD AND DEVICES FOR PERFORMING CARDIAC WAVEFORM APPRAISAL. If the preliminary analysis 208 reveals that the detected event 206 does not appear to be a cardiac event (or a cardiac event masked/covered by substantial noise), the detected event 206 is identified as a suspect event, and data associated with the detected event 206 is discarded, with the method then reverting back to the detection loop 200 using the same detection parameters that were previously in use. In some embodiments, step 208 may be omitted.

If preliminary analysis 208 is passed, then rhythm analysis is performed, as indicated at 210. Rhythm analysis may include any of a number of steps/methods. One illustrative example uses calculated heart rates and/or morphology analysis to create detected event markers that indicate whether a given detected event is "shockable" or "nonshockable". Morphology analysis may include, for example, comparison to a stored or dynamically changing template (for example, using correlation waveform analysis), QRS width analysis, and/or other shape-based analysis.

A buffer of shockable/nonshockable markers may be maintained as an X/Y counter. If a predetermined X/Y ratio is met, then the X/Y counter indicates therapy. For example, an 18/24 threshold may be used, where, if 18 of the previous 24 detected events that pass preliminary analysis are "shockable," the X/Y counter indicates therapy. The phrase "indicates therapy" is intended to mean that the implanted device has identified a treatable condition and therefore indicates that therapy is likely needed by the patient.

In addition, one or more persistence factors may be considered. Persistence may be observed by determining whether the X/Y counter indicates therapy for a threshold number of consecutive detected events. Illustrative examples of persistence analysis are set forth in commonly assigned US Patent Application Publication Number 2006-0167503, now U.S. Pat. No. 8,160,697, titled METHOD FOR ADAPTING CHARGE INITIATION FOR AN IMPLANTABLE CARDIOVERTER-DEFIBRILLATOR. For example, the persistence factor (if included) may call for the X/Y counter to indicate therapy for a minimum number, N (the persistence factor), of consecutive iterations. Where non-sustained tachycardias are identified, the persistence factor may be incremented to avoid shocking a non-sustained rhythm. In one example, N=2 initially and is increased by steps of 3 if/when nonsustained tachycardia occurs.

These methods are illustrative and no particular step is required to perform rhythm analysis 210.

Unless detection is suspended (for example, detection may be suspended during and shortly after a stimulus delivery or by a physician during telemetric communications with an implant), the method also performs steps to prepare for return to the detection loop 200. These steps may include determination of whether similar or dissimilar detected event peaks are observed, as shown at 212. The outcome of analysis at step 212 determines the detection profile configuration used to set the detection profile in step 214. The detection profile, as configured in step 214, is then used upon return to the detection loop 200.

The above examples of "similar" and "dissimilar" detection profile configurations may be used in step 214 to modify the detection profile. As shown by the examples of FIGS. 7A, step 214 may reduce the likelihood of persistent overdetection. This may, in turn, increase the accuracy of rhythm classification. As indicated by FIG. 7B, overdetection may occur even with step 214, however, because the modifications can reduce the frequency with which overdetections occur, the method helps avoid incorrect therapy decisions.

Figure 9:
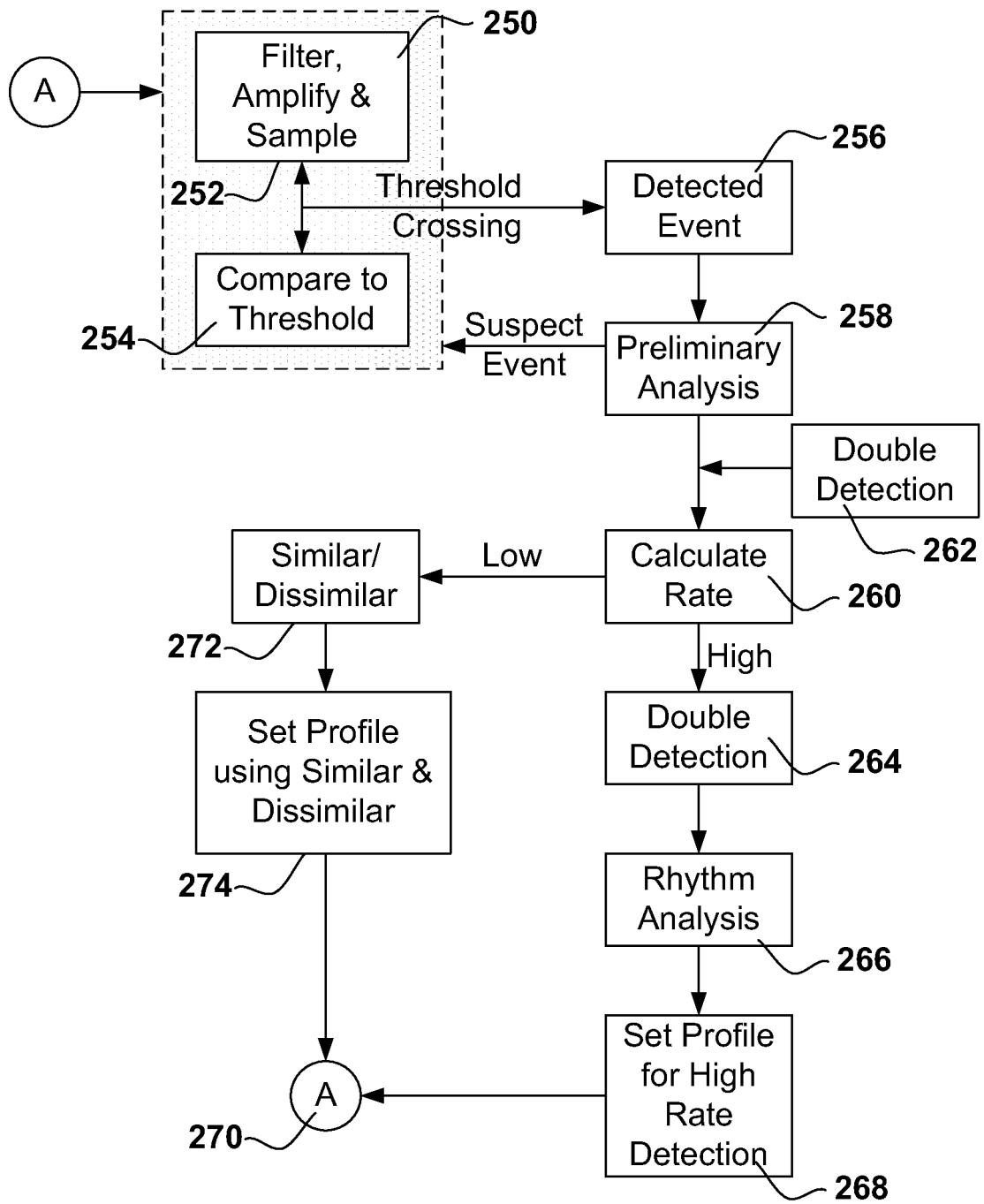
FIG. 9 is a flow diagram of another illustrative example of cardiac signal analysis in an implantable medical device.

FIG. 9 is a flow diagram of another illustrative example of cardiac signal analysis in an implantable medical device. A detection loop 250 is shown again including steps of filtering, amplifying and sampling 252 and comparing the captured signal to a threshold 254. A threshold crossing causes an exit from the detection loop 250, and a detected event is declared as shown at 256. Preliminary analysis 258 is again performed, as before, with noisy or suspect event identification causing a return to the detection loop 250.

If the preliminary analysis block 258 is passed, the method continues by calculating a heart rate, as indicated at 260. In some illustrative examples, double detection analysis may be performed prior to calculating heart rate, as noted at 262. Block 262 may be omitted, if desired.

Returning to step 260, if the heart rate is relatively high, the method continues by performing additional double detection analysis as shown at 264. The double detection analysis at 264 may be different and in addition to the analysis noted at 262. Double detection analysis 262, 264 may include any suitable method for identifying double detections. Some examples can be found in U.S. Provisional Patent Application No. 61/051332, titled METHODS AND DEVICES FOR IDEN- TIFYING AND CORRECTING OVERDETECTION OF CARDIAC EVENTS. The following are examples of analyses that may occur in blocks 262 or 264:

Identify High-Low-High correlation pattern(s) for detected events and correlation template(s).

Identify double detections resulting from multiple detections of wide cardiac complexes, which may include observation of whether pairs of detected events are very close together in time and have certain shape characteristics.

Identify Long-Short-Long interval pattern between detected events.

Other factors for identification of double detection (or of other overdetection such as triple detection) may instead be used, if desired, in step 262, 264.

Figure 11:
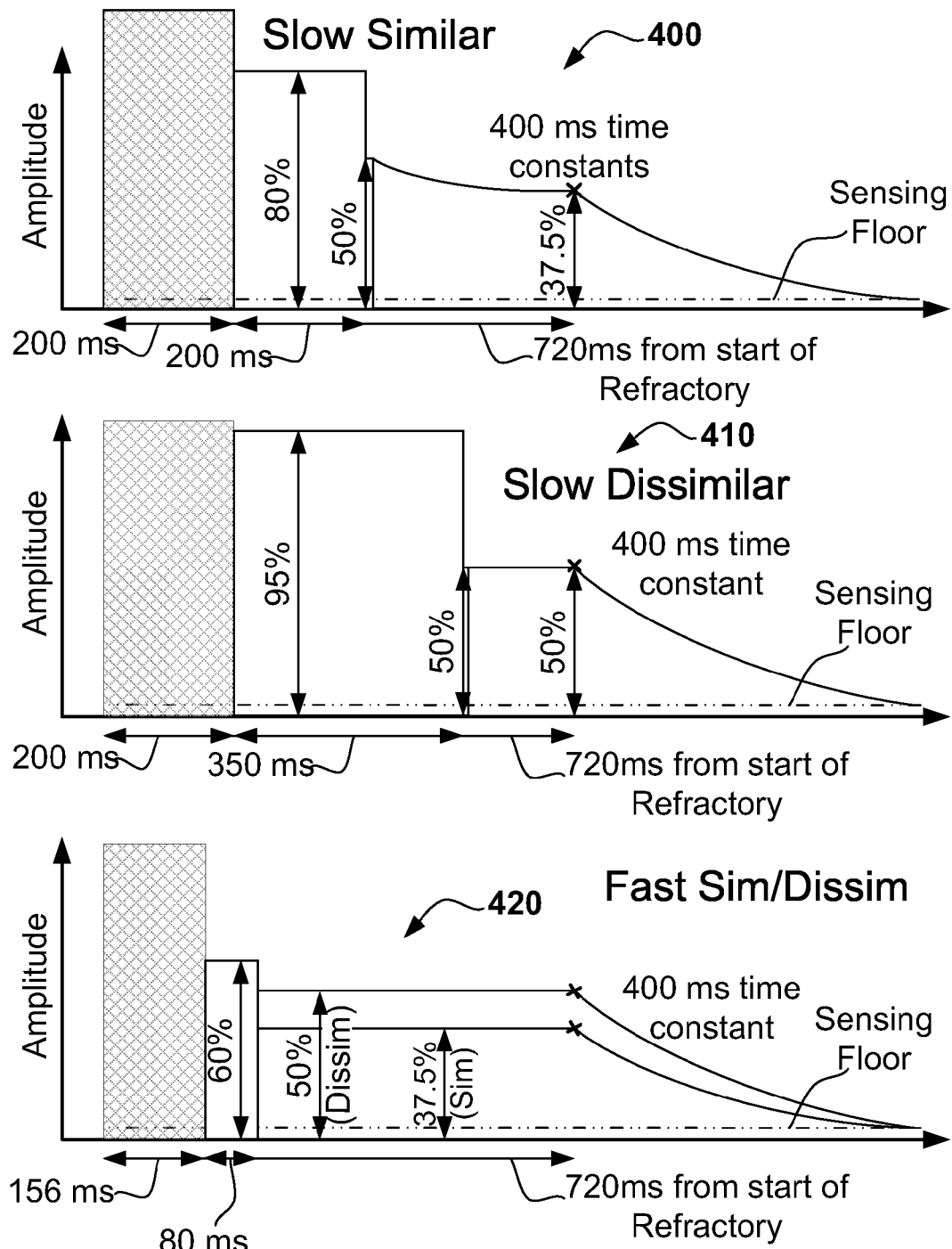
FIG. 11 illustrates a set of detection profiles and parameters for an illustrative example.
Figure 12:
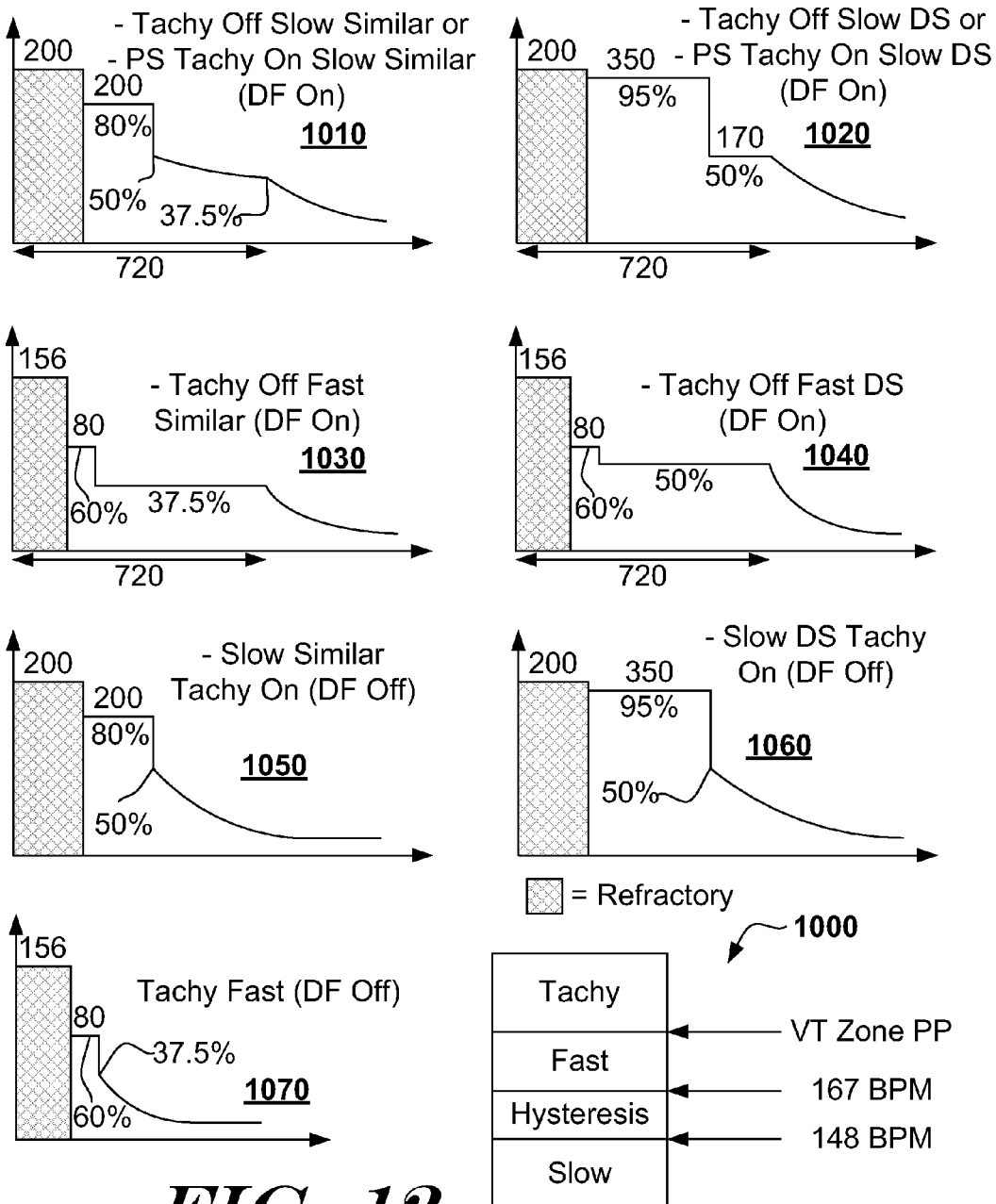
FIG. 12 illustrates a full set of detection profiles and parameters for another illustrative example.

Following block 264, rhythm analysis is performed as indicated at 266. Next, the detection profile is set, as shown at 268, using yet another detection profile configuration, this one being used when the calculated rate (step 260) is relatively high (FIGS. 11-12 show examples). The method then iterates at A 270.

If the heart rate is relatively low, the analysis determines whether detected event peaks are similar or dissimilar, as shown at 272. The method sets the detection profile using similarity/dissimilarity information, as shown at 274. The method next returns to the detection loop 250 via block A 270.

In an illustrative example, the "relatively low" and "relatively high" rates are calculated on the basis of an average of intervals between detected events that pass preliminary analysis 258 and, if included, the first pass of double detection analysis at 262.

In an illustrative example, the calculated rate is Low when a heart rate of less than about 148 bpm is calculated from an average of four intervals between detected events. Further in the illustrative example, the calculated rate is High when a heart rate greater than about 167 bpm is calculated. In the example, these values may lie on either side of a hysteresis band in which the characterization of "High" and "Low" rates depends upon the characterization of rate for the previous detected event. Thus, in the illustrative example, if the newly calculated rate is 155 bpm, and the previous rate was characterized as "High," then the rate is again characterized as "High". Other definitions of "High" and "Low" may be used and/or these values may be programmed during a telemetry session.

Figure 10:
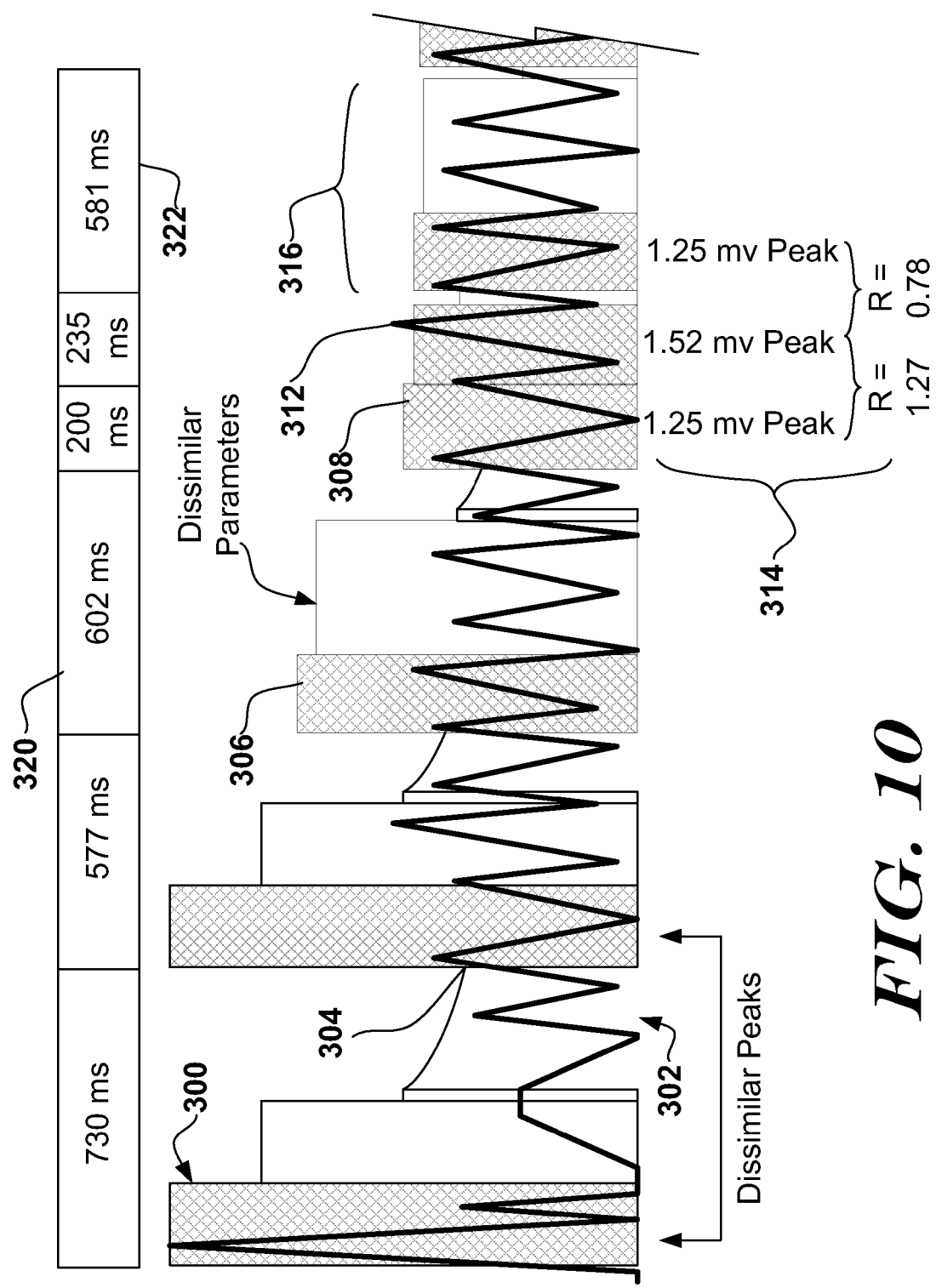
FIG. 10 illustrates detection using an illustrative example of detection profiles during onset of ventricular fibrillation.

In the illustrative example, the modifications to detection profile in view of similarity and dissimilarity are not used at step 268 for high rates. FIG. 10 provides an example showing how invocation of a "dissimilar" detection profile can slow the identification of a ventricular fibrillation. FIG. 11 provides illustrative examples of sets of parameters that may be used in the embodiment of FIG. 9 to define detection profiles. The addition of the fast detection profile parameters may avoid a delay in identification of a malignant rhythm shown in FIG. 10. FIG. 12 provides an even more detailed example.

The illustrative method of FIG. 9 uses computationally expensive "enhanced analysis" (at blocks 264 and 266) when calculated rates are relatively high, and simpler computations when calculated rates are relatively low. One example has been discussed above relative to FIG. 7B: a cardiac rhythm having an intrinsic rate of 100 cardiac cycles per minute included relatively large T-waves that caused overdetection. The cyclic invocation of the "dissimilar" detection profile configuration passes over the majority of the T-waves, resulting in a calculation of 133 bpm, rather than 200 bpm that would occur if each T-wave was counted. In the example, the peak ratio calculation allows use of detection profile modifications to reduce reliance on more computationally costly tools, potentially reducing power consumption.

FIG. 10 illustrates detection using an illustrative example of detection profiles during onset of ventricular fibrillation. A detection is shown at 300 with an R-wave peak occurring during the refractory period, and the detection profile easily passes over the following T-wave. For illustrative purposes, the detection profile following detection 300 is defined using "similar" peak parameters.

As shown at 302, the cardiac rhythm devolves into a ventricular fibrillation (VF), characterized by fast-moving, low amplitude peaks. The first detection of a VF peak occurs at 304. The amplitude for detection 304 is reduced significantly relative to peak 300. The system continues to use the same "similar" peak parameters based upon comparison of the detection at 300 to a prior peak. Another peak is detected at 306, with underdetection or "dropout" occurring for several VF Peaks. As indicated, based on the difference between peaks at detection 300 and detection 304, "dissimilar" parameters are used following detection 306. Due to averaging of the two prior detections, the estimated peak for detection 306 is still quite a bit higher than the current peak.

Continuing across FIG. 10, it can be seen that a VF peak is captured at 308, and is followed at 312 with another detected VF peak. In essence, the estimated peak measurement allows the detection profile to chase down the VF signal by lowering the amplitude of the highest portions of the detection profile as lower amplitude signals are captured.

VF is often inconsistent in amplitude and the baseline may wander. As a result, the use of the "dissimilar" profile may create additional problems with detection due to the intrinsic variability of VF. For example, the peak for detection 312 is higher than the peak for detection 308. As shown at 314, the variability yields peak ratios indicating that the peaks are "dissimilar." The dissimilar profile is then invoked as shown at 316. Because the dissimilar profile in this illustrative example is relatively less sensitive than the similar profile, this can delay further detections, as shown. One or more cardiac cycles can then go undetected by the implanted device. More underdetection may follow, since, as shown at 314, peak 312 is dissimilar from the following peak.

The upper portion of the Figure indicates detection intervals, at 320. As can be seen at 322, a relatively long interval is created by the dissimilar detection profile configuration. If an average of several intervals is used to estimate the heart rate of the implantee, a long interval caused by underdetection may throw several calculations into question. For at least this reason, the method of FIG. 9 may incorporate a fast tachy detection profile 1070 shown in FIG. 12.

FIG. 11 illustrates a set of detection profile configurations for an illustrative example. The detection profiles include a slow profile having similar and dissimilar variants 400, 410, and a fast profile 420 with similar and dissimilar variants. The variants on the fast profile 420 are shown together to simplify the illustration. In FIG. 11, the profiles are drawn to scale to show the differences in duration and in relative scaling of amplitudes. Refractory periods are shown with cross-hatching and have heights that correspond to an estimated peak.

In an illustrative example, "slow" means less than about 147 bpm, "fast" means greater than about 167 bpm, and a hysteresis band is used in between, in fashion similar to that explained above with reference to FIG. 9. In other examples, the hysteresis band may be larger, smaller, or omitted. The upper bound of "slow" may be anywhere in the range of 100-200 bpm, and the lower bound of "fast" may be in the range of, for example, 120-240 bpm, for example. These values may be modified further, if desired.

The illustrative slow similar profile 400 is for use when the calculated heart rate for the implantee is relatively slow and the peak amplitudes of a selected pair of detected events are similar to one another. The illustrative example uses a 200 millisecond refractory period, followed by a 200 millisecond first constant-threshold period at an amplitude of 80% of the estimated peak, followed by a 4 millisecond second constant threshold period at an amplitude of 50% of the estimated peak, followed by a first time-decaying portion starting at an amplitude of 50% of the estimated peak and decaying to 37.5% of the estimated peak using a time constant of 400 milliseconds. The first time-decaying portion of the illustrative slow similar profile 400 ends 720 milliseconds from the start of the refractory period and is followed by a second time-decaying portion that starts with an amplitude of 37.5% of the estimated peak and decays to the detection floor using a 400 millisecond time constant.

The illustrative slow dissimilar profile 410 is for use when the calculated rate for the implantee is relatively slow and the peak amplitudes of a selected pair of detected events are dissimilar from one another. The illustrative example uses a 200 millisecond refractory period, followed by a 350 millisecond first constant threshold period at an amplitude of 95% of the estimated peak, followed by a second constant threshold period having a duration of 4 milliseconds at an amplitude of 50% of the estimated peak. The first "decay" period is actually used as a continuation of the second constant threshold period, as there is no decay since the threshold remains at an amplitude of 50% of the estimated peak until expiration of the first decay period, which occurs 720 milliseconds after the beginning of the refractory period. A second time-decaying portion follows, beginning at an amplitude of 50% of the estimated peak and decaying to the detection floor using a 400 millisecond time constant.

The illustrative fast profile 420 is for use when the calculated rate in the implantee is relatively fast. For efficient illustration, both the similar and dissimilar profiles are shown at 420. The fast profile 420, in the illustrative example, includes a 156 millisecond refractory period followed by a first constant threshold portion having duration of 80 milliseconds and an amplitude of 60% of the estimated peak. The first constant threshold period is followed by a second constant threshold period having duration of 4 milliseconds with amplitude that varies in response to similarity/dissimilarity. A dynamic floor is also defined at the same amplitude as the second constant threshold period, such that the first "decay" time period actually does not decay.

When similar peaks are identified, the fast profile 420 uses 37.5% of the estimated peak for the second constant threshold period and the dynamic floor. When dissimilar peaks are identified, the fast profile 420 uses 50% of the estimated peak for the second constant threshold period and the dynamic floor.

The profiles are summarized here:

|  | Slow Dissim | Slow Similar | Fast Dissim | Fast Similar |
| --- | --- | --- | --- | --- |
| Ref (ms) | 200 | 200 | 156 | 156 |
| CT1 (%) | 95 | 80 | 60 | 60 |
| CT1 (ms) | 350 | 200 | 80 | 80 |
| CT2 (%) | 50 | 50 | 50 | 37.5 |
| CT2 (ms) | 4 | 4 | 4 | 4 |
| DF (%) | 50 | 37.5 | 50 | 37.5 |
| DFTO (ms) | 720 | 720 | 720 | 720 |
| Time Constant (ms) | 400 | 400 | 220 | 220 |

These values are merely illustrative of one embodiment, and may vary. In short, the method selects between a first pair of detection profiles when rates are relatively low, using peak similarity/dissimilarity to determine which profile to use. Further in the illustrative example, the method selects between a second pair of profiles when rates are relatively high, again using peak similarity/dissimilarity to determine which profile to use.

It can be seen in the illustrative example that the fast profiles 420 are more sensitive than the slow profiles, and the similar profiles are more sensitive than the dissimilar profiles. The greater sensitivity of the fast profiles 420 may help to track a malignant fast arrhythmia to relatively low amplitudes. This allows the detection profile to match the often low amplitude of malignant fast arrhythmia such as VF relatively quickly.

To illustrate, if an overdetection identification method uses pattern identification to determine that overdetection is occurring, detection profile manipulation that prevents some, but not all, overdetection may impede the pattern identification. Increasing sensitivity at high rates may avoid interference between the two system tools.

FIG. 12 illustrates a full set of detection profile configurations for another, detailed illustrative example. The level of detail in the example is not intended to limit the invention to any particular set of profiles and/or level of complexity. The illustrative example of FIG. 12 integrates several concepts including the use of multiple profiles, definition of fast and slow profiles, and the use of a tachyarrhythmia condition. Before explaining each profile, the sensing parameters including each of Tachy On/Off, and fast/slow are defined.

Tachy On/Off:

In the illustrative example, a tachycardia zone is defined for an implantable device as a programmable parameter. In particular, a physician or other user of the programmer 44 (FIG. 2) can set the lowest rate for which a tachycardia will be declared. Rates are shown graphically at 1000, with VT Zone PP representing the tachycardia zone programmable parameter. In the illustrative example, VT Zone PP can be set in a range of 170 bpm to 240 bpm. Any time the calculated rate for the illustrative example exceeds the VT Zone PP, a tachycardia condition is invoked.

Once a tachycardia condition is invoked, the device enters a "Tachy On" condition. The "Tachy On" condition remains in effect until the condition terminates. In an illustrative example, the Tachy On condition is terminated once a predetermined number of consecutive events are captured at a rate below the VT Zone PP rate. In a working embodiment, 24 consecutive rate calculations below VT Zone PP will terminate the Tachy On condition. An offset to the VT Zone PP may also be used to prevent toggling of Tachy On/Off, in addition to or as a substitute for the 24 consecutive calculations below VT Zone PP. Any time the "Tachy On" condition is not in effect, the device is in a "Tachy Off" condition.

Fast/Slow:

Next, with respect to definitions for Fast and Slow, a numeric example is shown at 1000. Rates below a low threshold are considered slow, and rates above a high threshold are considered fast in the illustrative embodiment. Rates between the thresholds fall within a hysteresis zone. When in the hysteresis zone, the rate is considered fast if the previous rate calculation was also considered fast, and slow if the previous rates calculation was considered slow. In the example, VT Zone PP is programmable to values that are above the high threshold. Therefore, some rates will be considered "Fast" but will not meet the criteria to create a "Tachy On" condition. Illustrative values for the high and low thresholds are shown as 148 and 167 bpm; the invention is not limited to these values. The 24 consecutive calculation rule used to determine the end of a Tachy On condition means that it is also possible to have a Slow rate while the "Tachy On" condition is still invoked.

Post-Shock Special Case:

Finally, a special case is encompassed by the illustrative example. In the illustrative example, data seeding occurs following delivery of a stimulus shock. This is disclosed in U.S. patent application Ser. No. 12/355,552, published as US Patent Application Publication Number 2009-0187227, titled DATA MANIPULATION FOLLOWING DELIVERY OF A CARDIAC STIMULUS IN AN IMPLANTABLE CARDIAC STIMULUS DEVICE. In addition to data seeding, the dynamic floor may be enabled, without changing the Tachy On condition. As a result, following delivery of a stimulus shock, the illustrative example enables the dynamic floor until a beat rate above VT Zone PP is calculated. As a result, post-shock sensing includes a special state in of Tachy On, Dynamic Floor On, referred to as the Post-Shock Tachy On condition.

With the above conditions set forth, the seven profiles shown in FIG. 12 can be explained as follows:

Detection profile 1010 is for use in the Tachy Off condition, as well as in the Post-Shock Dynamic Floor On condition when detected events display similar amplitudes.

Detection profile 1020 is for use in the Tachy Off condition, as well as in the Post-Shock Dynamic Floor On condition when detected events display dissimilar amplitudes.

Detection profile 1030 is for use in the Tachy Off condition where rates are Fast and detected events display similar amplitudes.

Detection profile 1040 is for use in the Tachy Off condition where rates are Fast and detected events display dissimilar amplitudes.

Detection profile 1050 is for use in the Tachy On condition where rates are slow and detected events display similar amplitudes.

Detection profile 1060 is for use in the Tachy On condition where rates are slow and detected events display dissimilar amplitudes.

Detection profile 1070 is for use in the Tachy On condition with fast rate.

As shown, the use of a dynamic floor in these detection profiles depends on whether a Tachy Off condition is occurring, except for the post-shock special case. As a result, profiles 1050, 1060 and 1070 do not show a dynamic floor. Instead, the first decay period is shown as decaying to the noise floor or sensing floor of the system.

As can be seen, the system allows for a large number of different variables to be manipulated. The following table provides numeric information for the illustrative example, with amplitudes provided as a percentage of estimated peak, and durations provided in milliseconds:

| Profile | 1010 | 1020 | 1030 | 1040 | 1050 | 1060 | 1070 |
|---|---|---|---|---|---|---|---|
| Ref (ms) | 200 | 200 | 156 | 156 | 200 | 200 | 156 |
| CT1 (ms) | 200 | 350 | 80 | 80 | 200 | 350 | 80 |
| CT1 (%) | 80 | 95 | 60 | 60 | 80 | 95 | 60 |
| CT2 (%) | 50 | 50 | 37.5 | 50 | 50 | 50 | 37.5 |
| DF (%) | 37.5 | 50 | 37.5 | 50 | * | * | * |
| DFTO (ms) | 720 | 720 | 720 | 720 | * | * | * |

FIG. 12 is intended to be an illustrative example, and the particular configurations, features and numeric examples shown are not intended to limit the present invention.

For any embodiment herein that makes reference to a decay period, any suitable shape may be used. In some examples, this may include exponential decay, any other asymptotic decay, or straight-line decay. Also, while the above embodiments refer to constant threshold periods, substituting a decay period is encompassed in additional embodiments. Ramping of the profile by increasing the threshold during a time period is another alternative that may replace decay or constant threshold periods.

While continuous or analog signals are shown in the illustrative examples, those of skill in the art will recognize the detection profile and/or captured signal may also be represented in the digital domain, such that a digital approximation of any of these decays is implemented.

As noted above, implantable devices typically use heart rate either alone or in conjunction with some other factor to determine whether the implantee needs therapy. "Some other factor" may include any suitable factor such as, for example, the morphology/shape of cardiac signals associated with detected events, and/or observation of any non-cardiac and/or non-electrical signal. An example of morphology analysis includes correlation analysis relative to a stored template representing a predetermined cardiac condition, such as a normal sinus rhythm or some predetermined arrhythmic condition such as atrial fibrillation. Difference of area and difference of squares are two forms of correlation analysis that may be performed. Other analysis, such as principle components analysis, source separation, wavelet transform and other mathematical analytics could also be performed as part of morphology analysis.

Some illustrative non-cardiac or non-electrical signals may include, for example, pulse oximetry data, patient respiration data, accelerometer data indicating patient movement, optical interrogation of blood composition, or any other suitable factor including measured temperature or blood pressure within an implantee. Some of these factors may be calculated using tissue impedance measurements. Non-cardiac signals may be used in several forms including, for example, to ensure that a captured electric signal is in fact a cardiac signal, or to inform decision making by providing an indication of patient status (for example, Is the patient's breathing accelerated, labored, normal, or stopped?, or Is the patient upright or laying down?). The present invention contemplates embodiments in which these additional factors, or any other suitable factor, are included in making stimulus delivery decisions.

The formula provided above for determining whether "similar" or "dissimilar" events are occurring is an illustrative example. The approach shown compares the two most recent peaks to determine whether they are similar. Other factors may be used. For example, a system may maintain statistics regarding prior peak activity or trend activity and may use the average or trend average and a standard deviation or variance to determine whether a newly detected event likely falls within "similar" or "dissimilar" bounds.

In yet another example, similar/dissimilar may be determined relative to the estimated peak, rather than the most recent peak. In another example, peak-to-peak ratios are calculated and recorded to generate statistics for peak ratios. An unexpected peak ratio outcome falling outside of statistical bounds may be considered as indicating dissimilarity.

Hysteresis may be built into the similar/dissimilar identification step. For example, a three part range for the peak ratio may be used as follows:

| Range | Outcome |
| --- | --- |
| Peak Ratio >1.3 or Peak Ratio <0.7 | Dissimilar |
| 0.9 < Peak Ratio <1.1 | Similar |
| Else | Same as Prior Outcome |

In this example, a hysteresis band is built into the peak ratio calculation.

Peak similarity is one method of determining whether consecutive detected events are similar or dissimilar. Another method may include morphological analysis. For example, two consecutive events may be analyzed by correlation waveform analysis to determine whether the two events are similar or dissimilar. In another example, a series of detected events may each be compared to a template to determine whether similarity or dissimilarity relative to the template occurs. In yet another example, rather than comparing two events to one another, events may be compared in a string of comparisons, for example, Event(n) may be compared to each of Event(n−1) and Event(n−2) to observe whether similar/dissimilar patterns emerge, likely indicating overcounting and, in the illustrative example, justifying the use of a less sensitive detection profile.

Given the nature of the comparisons taking place, it is also accurate to describe the comparison of a detected event to a previous detected event, either in simple amplitude or in morphology, as comparison of the detected event to stored data to determine the similarity of a most recent detected event to the stored data. The stored data may come from analysis of one or more prior events. This provides a more generic description of the underlying activity.

As noted above, other measures of estimated peak may also be used. The above examples simply average two prior peak amplitudes. The following are additional illustrative Estimated Peak calculations:

Est Peak [n]=Peak [n−1]

Est Peak [n]=(Peak [n−1]+Peak [n−2])/2

Est Peak [n]=(Peak [n−1]+Est Peak [n−1])/2

Where [n] represents the event under consideration, and [n−1, n−2] represent prior detected events. Other, more complex functions may be used. In another embodiment, the similarity/dissimilarity of a newly detected peak to the prior peak or estimated peak may be analyzed to determine whether to exclude the new detected peak from an updated calculation of estimated peak.

As noted above, various changes to the values provided, for example, with reference to FIGS. 7A-7B, the following ranges are illustrative:

|  | Dissimilar | Similar |
| --- | --- | --- |
| Refractory: | 50-350 ms | 50-250 ms |
| CT1 %: | 80-110% | 60-85% |
| CT1 Duration: | 0-400 ms | 0-300 ms |
| CT2 %: | 40-90% | 30-60% |
| CT2 Duration: | 0-200 ms | 0-200 ms |
| DF %: | 30-70% | 25-50% |
| DF TO: | 500-1500 ms from start of Refractory | |

Further, as discussed above, in addition to comparing the peak similarity or other characteristic of consecutive detections, the period between consecutive detections may also control which detection profile is invoked. In on example, if the period between two detections exceeds a threshold of, for example, 500-1000 ms, it is assumed that the detections do not originate in a single cardiac cycle, and a "Similar" detection profile is invoked.

Following are certain additional configuration examples:

EXAMPLE A:

|  | Dissimilar | Similar |
| --- | --- | --- |
| Refractory: | 150 ms | 150 ms |
| CT1 %: | 90% | 80% |
| CT1 Duration: | 200 ms | 200 ms |
| CT2 %: | 75% | 60% |
| CT2 Duration: | 300 ms | 20 ms |
| DF %: | 45% | 45% |
| DF TO: | 800 ms from start of Refractory | |

EXAMPLE B:

|  | Dissimilar | Similar |
| --- | --- | --- |
| Refractory: | 100 ms | 200 ms |
| CT1 Amplitude: | 80% | 80% |
| CT1 Duration: | 200 ms | 200 ms |
| CT2 Amplitude: | — | 50% |
| CT2 Duration: | — | 100 ms |
| DF %: | 35% | 35% |
| DTO: | 1250 ms from start of Refractory | |

Note in Example B, the CT2 component is excluded from the detection profile when dissimilar events are identified. Some embodiments incorporate this variation. In addition, the Dissimilar Profile is more sensitive here than the Similar profile, by virtue of a shorter refractory period and omission of the CT2 parameters. As noted above, this may encourage consistent overdetection that can be identified and corrected by other methods.

In some examples, the above configurations are modified in certain ways to incorporate the following form:

Threshold Amplitude=$P$ % of Est Peak+Constant

For example:

|  | Dissimilar | Similar |
| --- | --- | --- |
| Refractory: | 200 ms | 200 ms |
| CT1 %: | 80% + 25ADC | 80% |
| CT1 Duration: | 350 ms | 200 ms |
| CT2 %: | 50% + 25ADC | 50% |
| CT2 Duration: | 200 ms | 100 ms |

In this example, "25ADC" means twenty-five ADC units. Within this illustrative configuration, a maximum value for CT1 % and CT2 % may be set to the maximum dynamic range of the ADC output, or to some other predetermined maximum.

The above illustrative examples may be embodied in many suitable forms. Some embodiments will be method embodiments incorporating one or more of the above features/submethods in various combinations. Some embodiments will be devices adapted to perform the methods discussed above. Some embodiments will take the form of tangible media, such as magnetic, electric, or optical storage media, incorporating controller readable instruction sets. Some embodiments will take the form of or comprise controllers/microcontrollers associated with stored instruction sets for directing operations of various components in a device in accordance with one or more methods.

Briefly, an illustrative example may make use of a microcontroller-driven system which includes an input switch matrix for selecting one or more signal vectors as a sensing vector. The switch matrix leads to one or more amplifiers and filtering circuits that in turn couple to analog-to-digital conversion circuitry. Additional filtering of the incoming signal may be performed in the digital domain including, for example, 50/60 Hz notch filters. The incoming signal may then be analyzed using the microcontroller and any associated suitable registers and logic circuits. Some embodiments include, for example, dedicated hardware for peak or event detection and measurement, or for correlation waveform analysis.

In several illustrative examples, upon identification of a rhythm that indicates stimulus, a charging operation is undertaken. A sub-circuit for charging high-voltage or stimulus capacitors may have any suitable form. One example uses a charger taking the form of a flyback transformer circuit, a structure well known in the art. Any process and/or circuit that enables relatively low voltage batteries to charge capacitors to relatively high voltages may be used.

The device may further include output circuitry comprising, for example, an output H-bridge or modification thereof for controlling output polarity and duration from the high-power capacitor. Control circuitry associated with the H-bridge may be included, for example, to monitor or control current levels for constant current output signals or for performing diagnostic functions. The circuitry may be housed in a hermetically sealed canister.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable cardiac stimulus device (ICSD) comprising:
   a canister housing operational circuitry configured to perform cardiac signal analysis and configured to provide cardiac stimulus; and
   a lead electrode assembly coupled to the canister and operatively coupled to the operational circuitry;
   wherein a plurality of electrodes are provided on the lead electrode assembly and/or canister, the plurality of electrodes being coupled to the operational circuitry;
   wherein the operational circuitry is configured to perform a beat detection method comprising:
   capturing electrical signals from the electrodes;
   identifying events in the captured electrical signals using a detection profile, the detection profile providing a threshold having a threshold configuration for comparison to the captured signals such that, when the captured signals exceed the threshold, a detected event is declared;
   comparing a peak amplitude of a first detected event to a peak amplitude of a second detected event to determine whether the first and second events are similar or dissimilar; and
   if the first and second events are similar, using a first threshold configuration for detecting a subsequent event; or
   if the first and second events are dissimilar, using a second threshold configuration for detecting a subsequent event,
   wherein a sensitivity of the second threshold configuration is different than that of the first threshold configuration; and
   wherein the operational circuitry is further configured such that the first and second threshold configurations define at least the following time periods:
   a refractory period during which detected events are not declared;
   a constant threshold time period having a duration, CTD and an amplitude CTA; and
   a decay time period during which the threshold changes with time from a starting amplitude DTA;
   and further wherein the first threshold configuration has a longer CTD and higher CTA and DTA than the second threshold configuration.

2. The ICSD of claim 1 wherein the operational circuitry is further configured such that the first threshold configuration defines a more sensitive detection threshold than the second threshold configuration.

3. The ICSD of claim 1 wherein the operational circuitry is further configured such that the first threshold configuration defines a less sensitive detection threshold than the second threshold configuration.

4. The ICSD of claim 1 wherein the operational circuitry is also configured to perform a rhythm analysis method including the following steps:
   identify and mark detected events as either shockable or non-shockable;
   maintain an X/Y counter indicating how many detected events out of a set of detected events are marked as shockable;
   determine whether the X/Y counter indicates a malignant rhythm is occurring and, if so, whether the malignant rhythm has persisted for a predetermined number, N, of consecutive events;
   if the X/Y counter indicates a malignant rhythm, and the malignant rhythm has persisted for the predetermined number, N, of consecutive events, the operational circuitry is still further configured to begin charging a capacitor to a therapy voltage in preparation for stimulus delivery.

5. The ICSD of claim 1 wherein the operational circuitry is configured such that the values for CTA and DTA are defined as percentages of an estimated peak value for peaks identified in detected events.

6. An implantable cardiac stimulus device (ICSD) comprising:
   a canister housing operational circuitry configured to perform cardiac signal analysis and configured to provide cardiac stimulus; and
   a lead electrode assembly coupled to the canister and operatively coupled to the operational circuitry;
   wherein a plurality of electrodes are provided on the lead electrode assembly and/or canister, the plurality of electrodes being coupled to the operational circuitry;
   wherein the operational circuitry is configured to perform a beat detection method comprising:
   capturing electrical signals from the electrodes;

identifying events in the captured electrical signals using a detection profile, the detection profile providing a threshold having a threshold configuration for comparison to the captured signals such that, when the captured signals exceed the threshold, a detected event is declared;

comparing a peak amplitude of a first detected event to a peak amplitude of a second detected event to determine whether the first and second events are similar or dissimilar; and if the first and second events are similar, using a first threshold configuration for detecting a subsequent event; or if the first and second events are dissimilar, using a second threshold configuration for detecting a subsequent event, wherein a sensitivity of the second threshold configuration is different than that of the first threshold configuration;

wherein the operational circuitry is further configured such that the first and second threshold configurations define at least the following time periods:
- a refractory period during which detected events are not declared;
- a constant threshold time period with duration CTD and amplitude CTA;
- a time period during having start amplitude TSA, final amplitude TFA and a maximum duration MD; and
- a second decay time period during which the threshold changes over time from a decay starting amplitude DSA to a noise floor for the device;

and further wherein the first threshold configuration has a longer CTD and higher CTA, and TSA and TFA than the second threshold configuration.

7. A method of operation in an implantable cardiac stimulus system configured to detect cardiac events from an implanted location, the method incorporating a first detection threshold profile and a second detection threshold profile, both for use in detecting cardiac events, the method comprising a sim/dissim method of event detection comprising:

detecting a first detected event using one of the detection threshold profiles;

determining whether the first detected event is similar to or dissimilar from an amplitude measure of previous detected events; and:

if the first detected event is similar to the amplitude measure of previous detected events, using the first detection threshold profile to detect at least one subsequent event; or if the first detected event is dissimilar from the amplitude measure of previous detected events, using the second detection threshold profile to detect at least one subsequent event;

wherein the first and second detection threshold profiles differ in sensitivity;

wherein the detection threshold profiles used in the sim/dissim method of event detection comprise:
- a refractory period during which no events are declared;
- a constant threshold period having an amplitude CTA and a duration CTD; and
- a decay period having a starting amplitude DPSA and an ending amplitude at a sensing floor for the system;

wherein the second detection threshold profile has higher CTA and DPSA and a longer CTD than the first detection threshold profile.

8. The method of claim 7 wherein the first detection threshold profile is more sensitive than the second detection threshold profile.

9. The method of claim 7 wherein the first detection threshold profile is less sensitive than the second detection threshold profile.

10. The method of claim 7 wherein the detection threshold profiles used in the sim/dissim method each include an intermediate period that follows the constant threshold period and precedes the decay period and having a starting amplitude IPSA and an ending amplitude IPEA such that IPSA and IPEA for the first detection threshold profile are less than IPSA and IPEA for the second detection threshold profile.

11. The method of claim 10 wherein:
a fast rate detection threshold profile is also available for use in the system when an event rate above a rate threshold is identified;

the fast rate detection threshold profile includes a refractory period, a constant threshold period and a decay period, but no intermediate period; and CTA and DPSA are lower and refractory period and CTD are shorter for the fast rate detection threshold profile than for the detection threshold profiles used in the sim/dissim method.

12. The method of claim 11 further comprising:
estimating the cardiac rate of an implantee;

determining whether to use the fast rate detection threshold profile and, if so, using the fast rate detection threshold profile for detecting cardiac events and activating a method of identifying overdetected cardiac events; or else using the sim/dissim method for detecting cardiac events.

13. The method of claim 12 wherein the sim/dissim method further comprises selecting from among first, second, third and fourth detection profiles, the first and second detection profiles for use in a first rate zone, and third and fourth detection profiles for use in a second rate zone, both the first and second rate zones being below the fast rate causing use of the fast rate detection threshold profile, wherein the sim/dissim method selects between the third and fourth detection profiles using amplitude similarity/dissimilarity of detected events.

14. The method of claim 7 further comprising:
determining whether a high-rate malignant cardiac condition is occurring and, if so, delivering electrical stimulus to the patient to convert the high-rate malignant cardiac condition to a non-malignant condition.

15. An implantable cardiac stimulus device (ICSD) comprising a canister housing operational circuitry coupled to a plurality of electrodes, the canister being coupled to a lead electrode assembly having at least some of the plurality of electrodes disposed thereon, the operational circuitry being configured to perform a method comprising:

detecting cardiac events while implanted in a patient by capturing electrical signals and comparing captured electrical signals to a detection threshold;

determining whether a first detected event is similar in amplitude to a second detected event;

selecting a detection threshold configuration for use in subsequent event detection based on whether the first detected event is similar in amplitude to the second detected event wherein:

if the first and second detected events are similar in amplitude, a first detection threshold configuration is selected;

if the first and second detected events are not similar in amplitude, a second detection threshold configuration is selected; and detecting a subsequent event using a detection threshold defined by the selected detection threshold configuration and an estimated peak amplitude;

wherein the operational circuitry is further configured to include the following steps in the method:

detecting a plurality of detected events by repeatedly selecting detection threshold configurations based upon whether individual detected events are similar or dissimilar to one another in amplitude;

determining whether the plurality of detected events indicates a high-rate condition for the patient, and, if so, declaring a high-rate condition and selecting a third detection threshold configuration for use in detecting events while in the high-rate condition;

continuing to detect events if in the high-rate condition using the third detection threshold configuration until either:

the high-rate condition is found to be terminated; or the patient's cardiac condition is found to be malignant, upon which the ICSD prepares for and delivers a cardiac therapy to terminate the malignant condition.

16. The ICSD of claim 15 wherein the operational circuitry is configured such that the first detection threshold configuration has higher sensitivity than the second detection threshold configuration.

* * * * *